United States Patent
Weinbrenner et al.

(10) Patent No.: US 6,818,651 B2
(45) Date of Patent: Nov. 16, 2004

(54) (DIHYDRO) ISOQUINOLINE DERIVATIVES AS PHOSPHODIESTERASE INHIBITORS

(75) Inventors: Steffen Weinbrenner, Constance (DE); Beate Schmidt, Allensbach (DE); Gerhard Grundler, Constance (DE); Josef Stadlwieser, Constance (DE); Armin Hatzelmann, Constance (DE); Geert Jan Sterk, Utrecht (DE)

(73) Assignee: Altana Pharma AG, Constance (DE)

( * ) Notice: Subject to any disclaimer, the term of this patent is extended or adjusted under 35 U.S.C. 154(b) by 0 days.

(21) Appl. No.: 10/381,461

(22) PCT Filed: Nov. 8, 2001

(86) PCT No.: PCT/EP01/12918
§ 371 (c)(1),
(2), (4) Date: Aug. 21, 2003

(87) PCT Pub. No.: WO02/40450
PCT Pub. Date: May 23, 2002

(65) Prior Publication Data
US 2004/0044212 A1 Mar. 4, 2004

(30) Foreign Application Priority Data
Nov. 14, 2000 (EP) .............................. 00124774
Jan. 26, 2001 (DE) ........................... 101 03 547

(51) Int. Cl.$^7$ ............... A61K 31/472; C07D 217/14
(52) U.S. Cl. ................. 514/307; 546/144; 514/307
(58) Field of Search ......................... 546/144; 514/307

(56) References Cited

U.S. PATENT DOCUMENTS 6,043,263 A    3/2000  Bar et al. .................. 514/307

FOREIGN PATENT DOCUMENTS

| EP | 0 490 823 | 6/1992 |
| EP | 0 664 289 | 7/1995 |
| WO | 94/10118 | 5/1994 |
| WO | 89/08830 | 3/1998 |
| WO | 98/55481 | 12/1998 |
| WO | 99/44609 | 9/1999 |

OTHER PUBLICATIONS

Walker, K.A., et al. "1–(4–Aminobenzyl)– and 1–(4–Aminophenyl) isoquinoline Derivatives: Synthesis and Evaluation as Potential Irreversible Cyclic Nucleotide Phosphodiesterase Inhibitors", Journal of Medicinal Chemistry, vol. 26, No. 2, pp. 174–181, 1983.*

Caplus AN: 1999:123896, abstract of Fuhrmann, et al "Identification and function of cyclic nucleotide phosphodiesterase isoenzymes in airway epithelial cells," American Journal of Respiratory Cell and Molecular Biology (1999), 20(2), 292–302.*

Walker, K.A., et al., "1—(4–Aminobenzyl)—and 1—(4–Aminophenyl) isoquinoline Derivatives: Synthesis and Evaluation as Potential Irreversible Cyclic Neucleotide Phosphodiesterase Inhibitors", *Journal of Medicinal Chemistry*, vol. 26, No. 2, pp. 174–181, (1983).

Han, P., et al., "Alternative Splicing of the High Affinity CAMP–Specific Phosphodiesterase (*PDE7A*) mRNA in Human Skeletal Muscle and Heart", *Journal of Biological Chemistry*, vol. 272, No. 26, pp. 16152–16157, (1997).

Li, L., et al., "CD3– and CD28–Dependent Induction of PDE7 Required for T Cell Activation", Science, vol. 283, pp. 848–851, (Feb. 5, 1999).

Sasaki, T., et al., "Identification of Human PDE7B, a cAMP–Specific Phosphodiesterase", *Biochemical and Biophysical Research Communications*, vol. 271, No. 3, pp. 575–583, (2000).

St. Georgiev, V., et al., "Drug–Induced Modifications of the Immune Response. 1. Substituted 1–Phenylisoquinolines", *Journal of Medicinal Chemistry*, vol. 22, No. 4, pp. 348–352, (1979).

Michaeli, T., et al., "Isolation and Characterization of a Previously Undetected Human cAMP Phosphodiesterase by Complementation of cAMP Phosphodiesterase–deficient *Saccharomyces cerevisiae*", *The Journal of Biological Chemistry*, vol. 268, No. 17, pp. 12925–12932, (Jun. 15, 1993).

* cited by examiner

Primary Examiner—Ceila Chang
Assistant Examiner—Janet L. Coppins
(74) Attorney, Agent, or Firm—Nath & Associates PLLC; Todd L. Juneau; Sheldon M. McGee

(57) ABSTRACT

3,4-Dihydroisoquinoline and isoquinoline compounds of formula I, in which Ar represents a phenyl raidcal of the formulae IIa, IIb or IIc are novel effective PDE7 inhibitors.

19 Claims, No Drawings

(DIHYDRO) ISOQUINOLINE DERIVATIVES AS PHOSPHODIESTERASE INHIBITORS

USE OF THE INVENTION

The invention relates to novel phosphodiesterase inhibitors which are used in the pharmaceutical industry for producing drugs.

KNOWN TECHNICAL BACKGROUND

Journal of Medicinal Chemistry 1979, Vol. 22, No. 4, pp. 348–352 describes, inter alia, 6,7-dimethoxy-1-phenyl-3,4-dihydroisoquinolines which inhibit cAMP phosphodiesterases better than does the non-specific PDE inhibitor theophylline. In International Patent Application WO 99/44609 fused piperidine substituted arylsulfonamides are disclosed which are said to have potent activity in the treatment of Type II diabetes and obesity.

DESCRIPTION OF THE INVENTION

It has now been found that the compounds of the formula I, which are described in more detail below, possess surprising and particularly advantageous properties.

The invention relates to compounds of the formula I

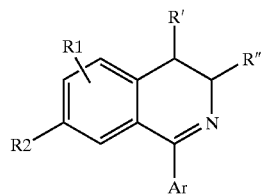

(I)

in which either
R1 denotes hydrogen, and
R2 denotes fluorine, chlorine, bromine, cyano, trifluoromethyl or phenoxy, or
R1 denotes hydrogen, fluorine, chlorine, bromine, trifluoromethyl or cyano, and
R2 denotes hydrogen,
R' and R" both denote hydrogen or together represent a bond, and
Ar represents a phenyl radical of the formulae IIa, IIb or IIc

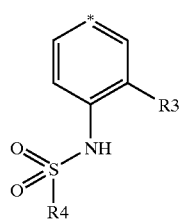

(IIa)

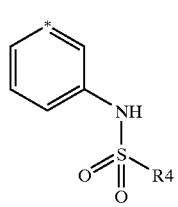

(IIb)

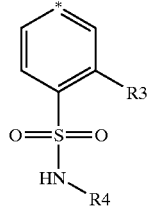

(IIc)

in which
R3 denotes hydrogen, hydroxyl, nitro, amino, carboxyl, aminocarbonyl, 1–4C-alkoxy, trifluoromethoxy, 1–4C-alkoxycarbonyl or mono- or di-1–4C-alkylaminocarbonyl,
R4 represents 1–4C-alkyl, naphthalenyl, 5-dimethylaminonaphthalen-1-yl, phenylethen-2-yl, 3,5-dimethylisoxazol-4-yl, 5-chloro-3-methylbenzo[b]thiophen-2-yl, 6-chloro-imidazo[2,1b]thiazol-5-yl, or represents a phenyl or thiophene radical which is unsubstituted or is substituted by one or more identical or different radicals selected from the group halogen, cyano, 1–4C-alkyl, trifluoromethyl, 1–4C-alkoxy which is substituted entirely or mainly by fluorine, 1–4C-alkoxy, 1–4C-alkylcarbonylamino, 1–4C-alkoxycarbonyl, phenylsulfonyl or isoxazolyl,
and also the salts of these compounds.

1–4C-alkyl represents a straight-chain or branched alkyl radical having 1 to 4 carbon atoms. The butyl, isobutyl, sec-butyl, tert-butyl, propyl, isopropyl and, preferably, the ethyl and methyl radicals may be mentioned by way of example.

1–4C-alkoxy represents radicals which, in addition to the oxygen atom, contain a straight-chain or branched alkyl radical having 1 to 4 carbon atoms. The butoxy, isobutoxy, sec-butoxy, tert-butoxy, propoxy, isopropoxy and, preferably, the ethoxy and methoxy radicals may be mentioned by way of example.

The 2,2,3,3,3-pentafluoropropoxy, perfluoroethoxy and 1,2,2-trifluoroethoxy radicals, in particular the 1,1,2,2-tetrafluoroethoxy, 2,2,2-trifluoroethoxy and trifluoromethoxy radicals and, preferably, the difluoromethoxy radical, may be mentioned as examples of 1–4C-alkoxy which is entirely or mainly substituted by fluorine. In this connection, "mainly" means that more than half of the hydrogen atoms are replaced with fluorine atoms.

1–4C-Alkoxycarbonyl represents a carbonyl group to which one of the abovementioned 1–4C-alkoxy radicals is bonded. The methoxycarbonyl [CH₃O—C(O)—] and the ethoxycarbonyl [CH₃CH₂O—C(O)—] radicals may be mentioned by way of example.

In addition to the nitrogen atom, mono- or di-1–4C-alkylamino radicals contain one or two of the abovementioned 1–4C-alkyl radicals. Examples which may be mentioned are the N-methyl-, N-ethyl, N-isopropyl-N,N-dimethyl- and N,N-diisopropylamino radical.

The propionylamino [C₃H₇C(O)NH—] radical and the acetylamino [CH₃C(O)NH—] radical may be mentioned as examples of the 1–4C-alkyl carbonyl amino radical.

In formulae IIa, IIb and IIc, * indicates the position in the phenyl radical at which the linking to the remainder of the molecule takes place.

Examples of substituted phenyl and thiophene radicals R4 which may be mentioned are 3,4-difluorophenyl, 2,5-difluorophenyl, 2,6-difluorophenyl, 3-trifluoromethylphenyl, 4-bromophenyl, 4-methylcarbonylaminophenyl, 4-tert-butylphenyl, 4-trifluoromethoxyphenyl, 2,5-dimethoxyphenyl, 3-chloro-2-methylphenyl, 2-trifluoromethoxyphenyl, 2-chloro-4-trifluoromethylphenyl, 2-chloro-4-fluorophenyl, 4-cyanophenyl, 4-methylphenyl, 4-n-butoxyphenyl, 5-isoxazol-3-ylthiophen-2-yl, 4-phenylsulfonylthiophen-2-yl, 4-bromo-2,5-dichlorothiophen-3-yl, 4-bromo-5-chlorothiophen-2-yl and 3-methoxy-4-methoxycarbonylthiophen-2-yl.

Depending on the substitution, all acid addition salts or all salts with bases are suitable salts for compounds of the formula I. Those which may particularly be mentioned are the pharmacologically tolerated salts of the inorganic and organic acids and bases which are customarily used in pharmacy. Suitable for use as such are, on the one hand, water-soluble and water-insoluble acid addition salts with acids such as hydrochloric acid, hydrobromic acid, phosphoric acid, nitric acid, sulfuric acid, acetic acid, citric acid, gluconic acid, benzoic acid, 2-(4-hydroxybenzoyl)benzoic acid, butyric acid, sulfosalicylic acid, maleic acid, lauric acid, maleic acid, fumaric acid, succinic acid, oxalic acid, tartaric acid, embonic acid, stearic acid, toluene sulfonic acid, methanesulfonic acid and 3-hydroxy-2-naphthoic acid, with the acids being employed, during the salt preparation, in an equimolar quantity ratio or in a quantity ratio which differs from this, depending on whether the acid is a monobasic or polybasic acid and depending on which salt is required.

On the other hand, salts with bases are also suitable. Examples of salts with bases which may be mentioned are alkali metal (lithium, sodium or potassium) salts, or calcium, aluminium, magnesium, titanium, ammonium, meglumin or guanidinium salts, with the bases being employed in this case, too, during the preparation of salt, in an equimolar quantity ratio or in a quantity ratio which differs from this.

Pharmacologically untolerated salts, which may, for example, initially accumulate as process products when preparing the compounds according to the invention on an industrial scale, are converted into pharmacologically tolerated salts using methods which are known to the skilled person.

The skilled person is familiar with the fact that the compounds according to the invention, and their salts, may contain varying quantities of solvents when, for example, they are isolated in crystalline form. The invention therefore also encompasses all solvates and, in particular, all hydrates of the compounds of the formula I and also all solvates and, in particular, all hydrates, of the salts of the compounds of the formula I.

One embodiment (embodiment a) of the invention are compounds of the formula I*

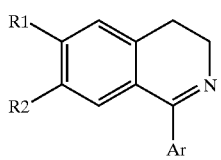

(I*)

in which either
R1 denotes hydrogen, and
R2 denotes fluorine, chlorine, bromine, cyano, trifluoromethyl or phenoxy, or
R1 denotes hydrogen, fluorine, chlorine, bromine, trifluoromethyl or cyano, and
R2 denotes hydrogen, and Ar represents a phenyl radical of the formulae IIa or IIb

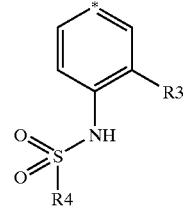

(IIa)

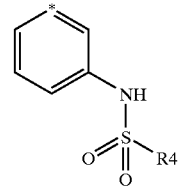

(IIb)

in which
R3 denotes hydrogen, hydroxyl, nitro, amino, carboxyl, aminocarbonyl, 1–4C-alkoxy, trifluoromethoxy, 1–4C-alkoxycarbonyl or mono- or di-1–4C-alkylaminocarbonyl,
R4 represents 1–4C-alkyl, naphthalenyl, 5-dimethylaminonaphthalen-1-yl, phenylethen-2-yl, 3,5-dimethylisoxazol-4-yl, 5-chloro-3-methylbenzo[b]thiophen-2-yl, 6-chloro-imidazo[2,1b]thiazol-5-yl, or represents a phenyl or thiophene radical which is unsubstituted or is substituted by one or more radicals selected from the group halogen, cyano, 1–4C-alkyl, trifluoromethyl, 1–4C-alkoxy which is substituted entirely or mainly by fluorine, 1–4C-alkoxy, 1–4C-alkylcarbonylamino, 1–4C-alkoxycarbonyl, phenylsulfonyl or isoxazolyl,
and also the salts of these compounds.

Another embodiment of the invention (embodiment b) are compounds of the formula I

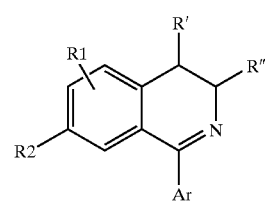

(I)

in which
R1 is in the 5-position and denotes fluorine, chlorine, bromine, trifluoromethyl or cyano, and
R2 denotes hydrogen,
R' and R" both denote hydrogen, and
Ar represents a phenyl radical of the formulae IIa or IIb

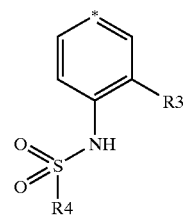

(IIa)

(IIb)

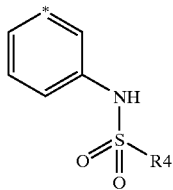

in which
R3 and R4 have the meanings given for embodiment a, and also the salts of these compounds.

Another embodiment of the invention (embodiment c) are compounds of the formula I (I)

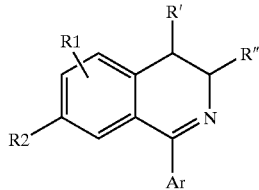

in which either
R1 denotes hydrogen, and
R2 denotes fluorine, chlorine, bromine, cyano, trifluoromethyl or phenoxy, or
R1 is in the 6-position and denotes hydrogen, fluorine, chlorine, bromine, trifluoromethyl or cyano, and
R2 denotes hydrogen,
R' and R" both denote hydrogen, and
Ar represents a phenyl radical of the formula IIc (IIc)

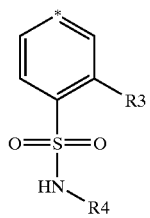

in which
R3 and R4 have the meanings given for embodiment a, and also the salts of these compounds.

Another embodiment of the invention (embodiment d) are compounds of the formula I (I)

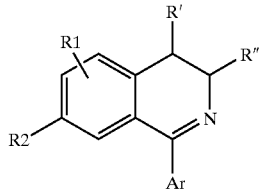

in which either
R1 denotes hydrogen, and
R2 denotes fluorine, chlorine, bromine, cyano, trifluoromethyl or phenoxy, or
R1 is in the 6-position and denotes hydrogen, fluorine, chlorine, bromine, trifluoromethyl or cyano, and
R2 denotes hydrogen and
R' and R" together represent a bond to give compounds of the following formula

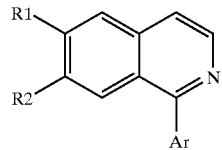

and
Ar represents a phenyl radical of the formulae IIa or IIb (IIa)

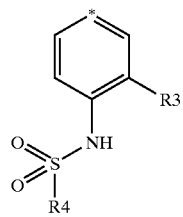

(IIb)

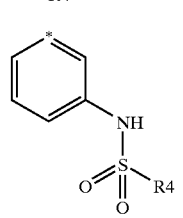

in which
R3 and R4 have the meanings given for embodiment a, and also the salts of these compounds.

Compounds of the formula I which are to be emphasized are those in which either
R1 denotes hydrogen, and
R2 denotes fluorine, chlorine or phenoxy, or
R1 denotes hydrogen, fluorine, chlorine or trifluoromethyl, and
R2 denotes hydrogen,
R' and R" both denote hydrogen or together represent a bond, and
Ar represents a phenyl radical of the formulae IIa, IIb or IIc,
in which
R3 denotes hydrogen, hydroxyl or 1–4C-alkoxy,
R4 denotes 1–4C-alkyl, naphthalenyl, 5-dimethylamino-naphthalen-1-yl, phenylethen-2-yl, 3,5-dimethylisoxazol-4-yl, 5-chloro-3-methylbenzo[b]thiophen-2-yl, 6-chloro-imidazo[2,1b]thiazol-5-yl, or represents a phenyl or thiophene radical which is unsubstituted or is substituted by one or more identical or different radicals selected from the group halogen, cyano, 1–4C-alkyl, trifluoromethyl, 1–4C-alkoxy which is substituted entirely or mainly by fluorine, 1–4C-alkoxy, 1–4C-alkylcarbonylamino, 1–4C-alkoxycarbonyl, phenylsulfonyl or isoxazolyl,
and also the salts of these compounds.

Compounds of the formula I which are to be particularly emphasized are those in which either R1 denotes hydrogen, and R2 denotes fluorine, chlorine or phenoxy, or R1 denotes hydrogen, fluorine, chlorine or trifluoromethyl, and R2 denotes hydrogen, R' and R" both denote hydrogen or together represent a bond, and Ar represents a phenyl radical of the formulae IIa, IIb or IIc, in which R3 denotes hydrogen, hydroxy or methoxy, R4 denotes isopropyl, naphthalen-2-yl, 5-dimethylaminonaphthalen-1-yl, phenylethen-2-yl, 3,5-dimethylisoxazol-4-yl, 5-chloro-3-methylbenzo[b]thiophen-2-yl, 6-chloro-imidazo[2,1b]thiazol-5-yl, 3,4-difluorophenyl, 2,6-difluorophenyl, 3-trifluoromethyl-phenyl, 4-bromophenyl, 4-tert-butylphenyl, 4-trifluoromethoxyphenyl, 2,5-dimethoxyphenyl, 3-chloro-2-methylphenyl, 2-trifluoromethoxyphenyl, 2-chloro4-trifluoromethylphenyl, 2-chloro4-fluorophenyl, 4-cyanophenyl, 4-methylphenyl, 4-n-butoxyphenyl, 5-isoxazol-3-yl-thiophen-2-yl, 4-phenylsulfonylthiophen-2-yl, 4-bromo-2,5-dichlorothiophen-3-yl, 4-bromo-5chlorothiophen-2-yl, or 3-methoxy-4-methoxycarbonylthiophen-2-yl, and also the salts of these compounds.

Preferred compounds of the formula I are those in which

R1 denotes hydrogen, and

R2 denotes fluorine or chlorine,

R' and R" both denote hydrogen, and

Ar represents a phenyl radical of the formula IIa, in which

R3 denotes hydroxyl or methoxy,

R4 denotes isopropyl, naphthalen-2-yl, 5-dimethylaminonaphthalen-1-yl, phenylethen-2-yl, 3,5-dimethylisoxazol-4-yl, 5-chloro-3-methylbenzo[b]thiophen-2-yl, 6-chloro-imidazo[2,1b]thiazol-5yl, 3,4-difluorophenyl, 2,6-difluorophenyl, 3-trifluoromethyl-phenyl, 4-bromophenyl, 4-methylcarbonylamino-phenyl, 4-tert-butylphenyl, 4-trifluoromethoxyphenyl, 2,5-dimethoxyphenyl, 3-chloro-2-methylphenyl, 2-trifluoromethoxyphenyl, 2-chloro4-trifluoromethylphenyl, 2-chloro4-fluorophenyl, 4-cyanophenyl, 4-methylphenyl, 4-n-butoxyphenyl, 5-isoxazol-3-yl-thiophen-2-yl, 4-phenylsulfonylthiophen-2-yl, 4-bromo-2,5-dichlorothiophen-3-yl, 4-bromo-5-chlorothiophen-2-yl or 3-methoxy-4-methoxycarbonylthiophen-2-yl, and also the salts of these compounds.

The reaction scheme 1 shows, by way of example, how the compounds of the formula I according to the invention with Ar being a phenyl radical of the formulae IIa or IIb can be prepared. Proceeding from suitably substituted phenyl-ethyl amines (compounds of the formula VIII), an acylation with para-nitro- or meta-nitro benzoic acid derivatives (compounds of formulae VIIa and VIIb) is carried out in a first step.

The acylation can be carried out using all known acylation methods, such as activating the acid group by converting it into the acid chloride or an acid anhydride, or else using the known amide coupling reagents such as dicyclohexylcarbodiimide, diisopropylcarbodiimide and N-dimethyl-aminoethyl-N'-ethylcarbodiimide, etc.

In a second step, the isoquinoline ring system is constructed by means of a cyclocondensation reaction. The cyclocondensation is effected in a manner known to the skilled person, for example as described by Bischler-Napieralski (J. Chem. Soc., 1956, 4280–4282) in the presence of a suitable condensing agent, such as polyphosphoric acid, phosphorus pentachloride, phosphorus pentoxide or, preferably, phosphorus oxytrichloride, in a suitable inert solvent, for example in a chlorinated hydrocarbon such as chloroform, or in a cyclic hydrocarbon, such as toluene or xylene, or another inert solvent, such as acetonitrile, or without any further solvent using an excess of condensing agent, preferably at elevated temperature, in particular at the boiling temperature of the solvent and/or condensing agent employed.

Reaction Scheme 1:

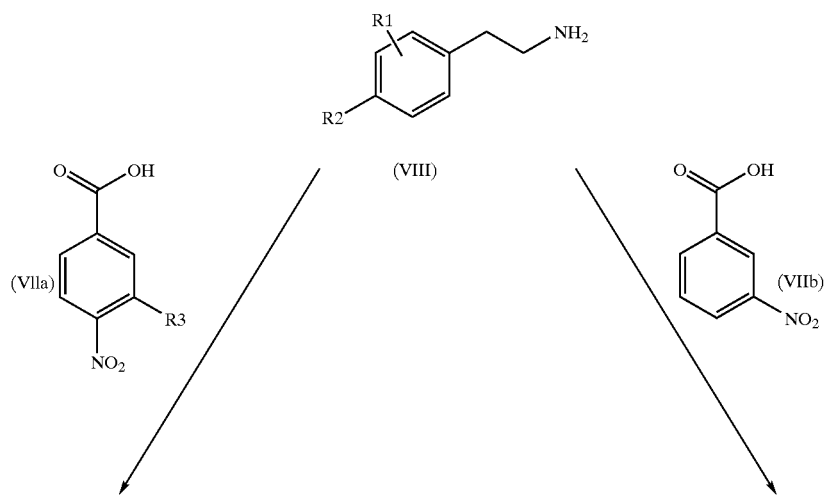

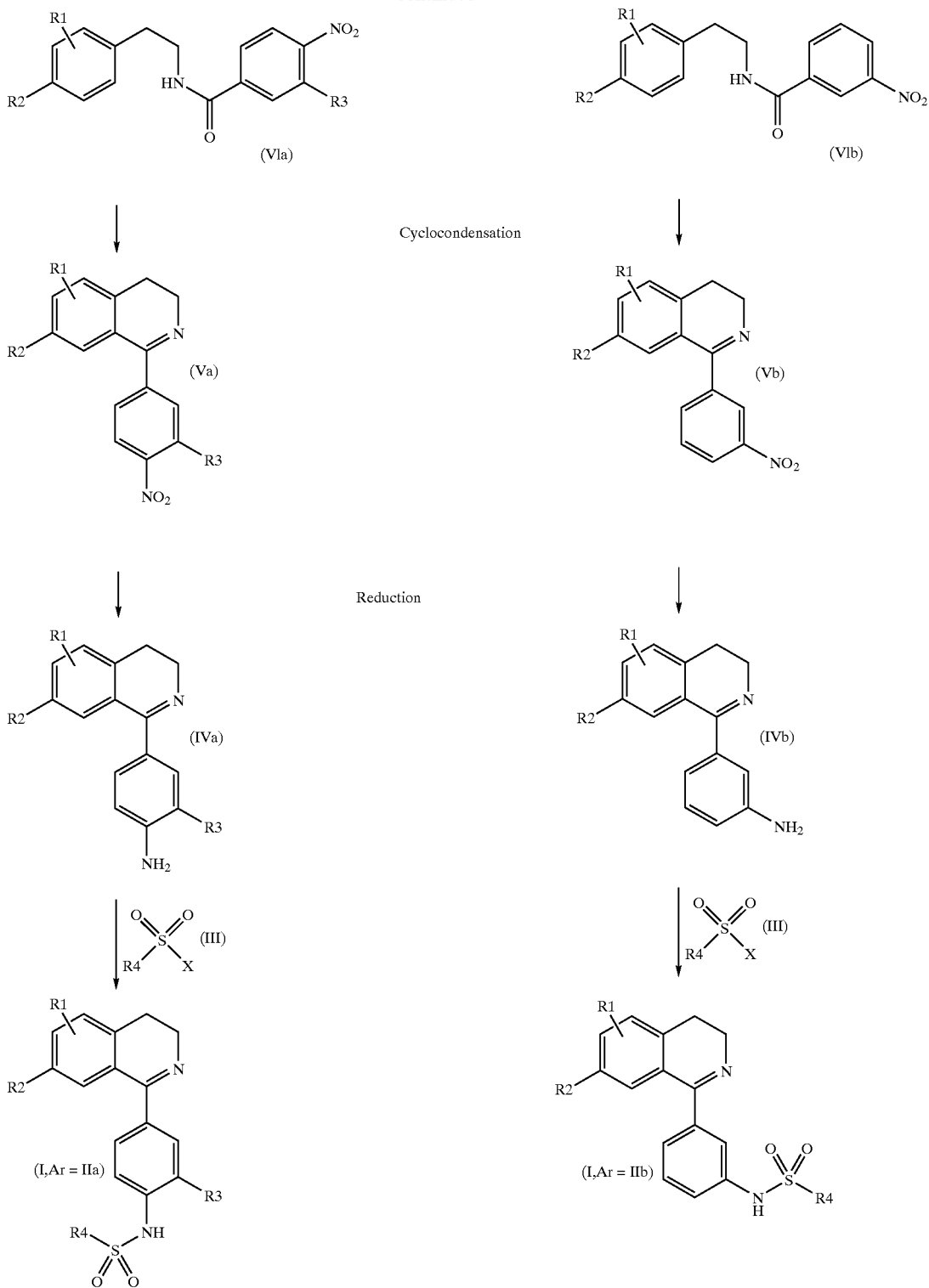

-continued

Cyclocondensation

Reduction

The resulting nitro-substituted isoquinoline derivatives (compounds of the formula Va and Vb) are subsequently converted into the corresponding amino-substituted isoquinoline derivatives (compounds of the formulae IVa and IVb) by using selective reduction methods.

Examples of suitable selective reduction methods which may be mentioned are various metal/acid systems, such as Fe/HOAc or $SnCl_2$/HCl, or else catalytic hydrogenation. The reduction is preferably effected by means of catalytic transfer hydrogenation using ammonium formate and palladium on charcoal (e.g. as described in the examples below).

The reaction of the amino-substituted isoquinoline derivatives (compounds of the formulae IVa and IVb) with sulfonic acid derivatives R4-S(O)$_2$—X (compounds of the formula III), in which X represents a suitable leaving group, preferably a chlorine atom, finally yields the compounds of the formula I according to the invention.

The reaction scheme 2 shows exemplary how the compounds of formula I according to the invention with Ar being a phenyl radical of the formula IIc can be prepared.

The following examples serve to clarify the invention without restricting it. Other compounds of the formula I, whose preparation is not explicitly described, can also be prepared in an analogous manner, or in a manner with which the skilled person is familiar, using customary process technology.

Reaction Scheme 2:

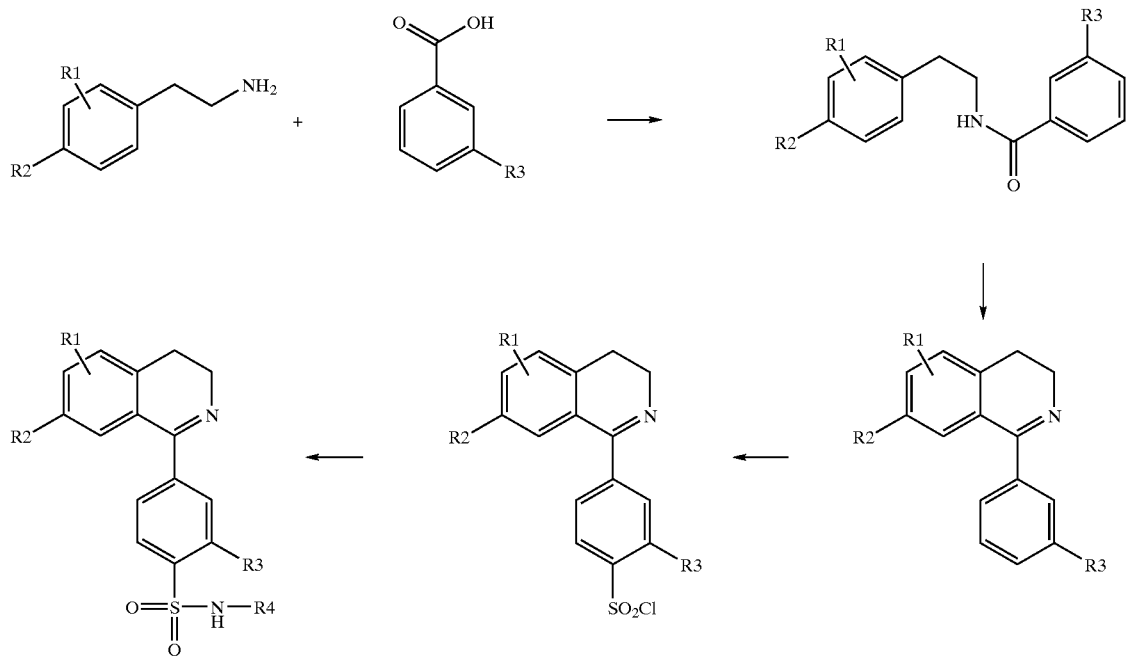

The acylation and subsequent cyclocondensation outlined in the above scheme is carried out under similar conditions as specified for scheme 1. The sulfochlorination is effected in a manner known to the expert, e. g. with chlorosulfuric acid in methylene chloride at 0° C. The last step in the above reaction sequence is preferably carried out in an inert solvent under basic conditions, for example in the presence of an auxiliary inorganic base, such as sodium or potassium carbonate, or with an excess of the amine R4-NH$_2$.

In the above reaction schemes 1 and 2, the synthesis of compounds of the formula I, wherein R' and R" both denote hydrogen, is outlined. Compounds in which R' and R" together represent a bond are obtained by selective oxidation, e. g. as described in the examples.

Salts are obtained by dissolving the free compound in a suitable solvent (e.g. a ketone, such as acetone, methyl ethyl ketone or methyl isobutyl ketone, an ether, such as diethyl ether, tetrahydrofuran or dioxane, a chlorinated hydrocarbon, such as methylene chloride or chloroform or a low molecular weight aliphatic alcohol, such as ethanol or isopropanol (which contains the desired acid or base, or to which the desired acid or base is subsequently added. The salts are isolated by filtering, reprecipitating, precipitating with what is a non-solvent for the addition salt, or by evaporating off the solvent. Salts which have been obtained can be converted into the free compounds by alkalinizing or acidifying, with it then being possible to convert the free compounds into salts once again. In this way, salts which are not pharmacologically tolerated can be converted into salts which are pharmacologically tolerated.

The following methods were used for characterizing the compounds:

MS: atmospheric pressure chemical ionization mass spectrometry (APCI-MS) or electron impact ionization mass spectrometry (EI-MS).

HPLC: A Superspher 60 RP-Select B 75×4 mm column from Merck was used; the chromatography was carried out at a column temperature of 40° C. using a flow of 1 ml/min. The solvent system employed was solvent A (water+0.5% trifluoroacetic acid) and solvent B (acetonitrile+0.5% trifluoroacetic acid), with the following gradient course being used:

| min | % A | % B |
|---|---|---|
| 0.0 | 80 | 20 |
| 2.0 | 80 | 20 |
| 6.0 | 30 | 70 |
| 8.0 | 30 | 70 |
| 10.0 | 80 | 20 |
| 11.0 | 80 | 20 |

Detection was carried out by UV at 254 nm.

In the examples, calc. stands for calculated, f. stands for found, RT is room temperature and h stands for hour(s). The compounds mentioned in the examples, and their salts, are preferred subject-matter of the invention.

EXAMPLES

End Products 1a. 1-[4-(4-Trifluoromethoxybenzenesulfonamido)-3-methoxyphenyl]-7-chloro-3,4-dihydroisoquinoline 28.7 mg of 1-(4-amino-3-methoxyphenyl)-7-chloro-3,4-dihydroisoquinoline are dissolved in 400 μl of dioxane, and 300 μl of a 0.33 molar solution of sodium carbonate are then added. 480 μl of a 0.25 molar solution of 4-trifluoromethoxybenzenesulfonyl chloride in dioxane are added to this mixture. The whole is stirred at RT for 16 h and the reaction mixture is loaded, at neutral pH, onto a cartridge containing 400 mg of diatomaceous earth and 300 mg of alumina. The product is eluted with 12 ml of dichloromethane. The eluate is concentrated and the residue is purified by flash chromatography on silica gel. 34 mg of the title compound are obtained.

$^1$H NMR (200 MHz, D$_6$-DMSO): δ=2.71 (m,2H), 3.48 (s,3H), 3.71 (m,2H), 7.02–7.08 (m,3H), 7.34 (d,J=8.0 Hz,1H), 7.40 (d,J=8.1 Hz,1H), 7.49–7.54 (m,2H), 7.58 (s,1H), 7.85 (m,1H), 7.89 (m,1H), 9.86 (s,1H).

MS: calc.: $C_{23}H_{18}ClF_3N_2O_4S$ (510.92) f.: [M+1] 511.0 HPLC[min]: 7.41

The following are obtained in accordance with this procedure:

1b. 1-[4-(4-Methylbenzenesulfonamido)-3-methoxyphenyl]-7-chloro-3,4-dihydroisoquinoline
MS: calc.: $C_{23}H_{21}ClN_2O_3S$ (440.95) f.: [M+1] 441.0 HPLC[min]: 7.07

1c. 1-[4-(4-Bromo-5-chlorothophene-2-sulfonamido)-3-methoxyphenyl]-7-chloro-3,4-dihydroisoquinoline
MS: calc.: $C_{20}H_{15}BrCl_2N_2O_3S_2$ (546.29) f.: [M+1] 546.9 HPLC[min]: 7.52

1d. 1-[4-(Naphthalene-2-sulfonamido)-3-methoxyphenyl]-7-chloro-3,4-dihydroisoquinoline
MS: calc.: $C_{26}H_{21}ClN_2O_3S$ (476.99) f.: [M+1] 477.0 HPLC[min]: 7.33

1e. 1-[4-(4-Benzenesulfonylthiophene-2-sulfonamido)-3-methoxyphenyl]-7-chloro-3,4-dihydroisoquinoline
MS: calc.: $C_{26}H_{21}ClN_2O_5S_3$ (573.11) f.: [M+1] 573.1 HPLC[min]: 7.07

1f. 1-[4-(3-Trifluoromethylbenzenesulfonamido)-3-methoxyphenyl]-7-chloro-3,4-dihydroisoquinoline
MS: calc.: $C_{23}H_{18}ClF_3N_2O_3S$ (494.92) f.: [M+1] 495.0 HPLC[min]: 7.33

1g. 1-[4-(5-(Isoxazol-3-yl)-thiophene-2-sulfonamido)-3-methoxyphenyl]-7-chloro-3,4-dihydroisoquinoline
MS: calc.: $C_{23}H_{18}ClN_3O_4S_2$ (500.0) f.: [M+1] 500.0 HPLC[min]: 6.91

2a. 1-[4-(5-(Isoxazol-3-yl)-thiophene-2-sulfonamido)-3-methoxyphenyl]-3,4-dihydroisoquinoline
MS: calc.: $C_{23}H_{19}N_3O_4S_2$ (465.55) f.: [M+1] 466.0 HPLC[min]: 6.75

2b. 1-[4-(3-Trifluoromethylbenzenesulfonamido)-3-methoxyphenyl]-3,4-dihydroisoquinoline
MS: calc.: $C_{23}H_{19}F_3N_2O_3S$ (460.48) f.: [M+1] 461.0 HPLC[min]: 7.09

2c. 1-[4-(4-Benzenesulfonylthiophene-2-sulfonamido)-3-methoxyphenyl]-3,4-dihydroisoquinoline
MS: calc.: $C_{26}H_{22}N_2O_5S_3$ (538.67) f.: [M+1] 539.1 HPLC[min]: 6.96

2d. 1-[4-(Naphthalene-2-sulfonamido)-3-methoxyphenyl]-3,4-dihydroisoquinoline
MS: calc.: $C_{26}H_{22}N_2O_3S$ (442.54) f.: [M+1] 443.1 HPLC[min]: 7.12

2e. 1-[4-(4-Bromo-5-chlorothiophene-2-sulfonamido)-3-methoxyphenyl]-3,4-dihydroisoquinoline
MS: calc.: $C_{20}H_{16}BrClN_2O_3S_2$ (511.85) f.: [M+1] 512.9 HPLC[min]: 7.31

2f. 1-[4-(4-Methylbenzenesulfonamido)-3-methoxyphenyl]-3,4-dihydroisoquinoline
MS: calc.: $C_{23}H_{22}N_2O_3S$ (406.51) f.: [M+1] 407.1 HPLC[min]: 6.80

2g. 1-[4-(4-Trifluoromethoxybenzenesulfonamido)-3-methoxyphenyl]-3,4-dihydroisoquinoline
MS: calc.: $C_{23}H_{19}F_3N_2O_4S$ (476.48) f.: [M+1] 477.1 HPLC[min]: 7.20

3a. 1-[4-(3,4-Difluorobenzenesulfonamido)phenyl]-6-fluoro-3,4-dihydroisoquinoline
MS: calc.: $C_{21}H_{15}F_3N_2O_2S$ (416.43) f.: [M+1] 417.1 HPLC[min]: 5.37

3b. 1-[4-(3,5-Dimethylisoxazole-4-sulfonamido)phenyl]-6-fluoro-3,4-dihydroisoquinoline
MS: calc.: $C_{20}H_{18}FN_3O_3S$ (399.45) f.: [M+1] 400.0 HPLC[min]: 3.95

3c. 1-[4-(3-Trifluoromethylbenzenesulfonamido)phenyl]-6-fluoro-3,4-dihydroisoquinoline
MS: calc.: $C_{22}H_{16}F_4N_2O_2S$ (448.44) f.: [M+1] 449.1 HPLC[min]: 6.29

3d. 1-[4-(Naphthalene-2-sulfonamido)phenyl]-6-fluoro-3,4-dihydroisoquinoline
MS: calc.: $C_{25}H_{19}FN_2O_2S$ (430.5) f.: [M+1] 431.1 HPLC[min]: 6.20

3e. 1-[4-(4-tert-Butylbenzenesulfonamido)phenyl]-6-fluoro-3,4-dihydroisoquinoline
MS: calc.: $C_{25}H_{25}FN_2O_2S$ (436.55) f.: [M+1] 437.2 HPLC[min]: 7.27

3f. 1-[4-(2-Phenylethensulfonamido)phenyl]-6-fluoro-3,4-dihydroisoquinoline
MS: calc.: $C_{23}H_{19}FN_2O_2S$ (406.48) f.: [M+1] 407.1 HPLC[min]: 5.77

3g. 1-[4-(4-Trifluoromethoxybenzenesulfonamido)phenyl]-6-fluoro-3,4-dihydroisoquinoline
MS: calc.: $C_{22}H_{16}F_4N_2O_3S$ (464.44) f.: [M+1] 465.1 HPLC[min]: 6.64

3h. 1-[4-(5-Chloro-3-methylbenzo[b]thiophene-2-sulfonamido)phenyl]-6-fluoro-3,4-dihydroisoquinoline
MS: calc.: $C_{24}H_{18}ClFN_2O_2S_2$ (485.0) f.: [M+1] 485.1 HPLC[min]: 7.61

3i. 1-[4-(4-Methylbenzenesulfonamido)phenyl]-6-fluoro-3,4-dihydroisoquinoline
MS: calc.: $C_{22}H_{19}FN_2O_2S$ (394.47) f.: [M+1] 395.1 HPLC[min]: 5.25

3k. 1-[14-(2,5-Dimethoxybenzenesulfonamido)phenyl]-6-fluoro-3,4-dihydroisoquinoline
MS: calc.: $C_{23}H_{21}FN_2OS$ (440.50) f.: [M+1] 441.1 HPLC[min]: 4.81

3l. 1-[4-(4-Brom-2,5-dichlor thi phene-3-sulfonamido)phenyl]-6-fluoro-3,4-dihydro is oquinoline
MS: calc.: $C_{19}H_{12}BrCl_2FN_2O_2S_2$ (534.26) f.: [M+1] 534.9 HPLC[min]: 6.21

3m. 1-[4-(4-Bromo-5chlorothiophen-2-sulfonamido)phenyl]-6-fluoro-3,4-dihydroisoquinoline
MS: calc.: $C_{19}H_{13}BrClFN_2O_2S_2$ (499.81) f.: [M+1] 501.0 HPLC[min]: 6.73

3n. 1-[4-(2-Methyl-3chlorobenzenesulfonamido)phenyl]-6-fluoro-3,4-dihydroisoquinoline
MS: calc.: $C_{22}H_{18}ClFN_2O_2S$ (428.92) f.: [M+1] 429.1 HPLC[min]: 6.16

3o. 1-[4-(2-Chloro-4-trifluoromethylbenzenesulfonamido)phenyl]-6-fluoro-3,4-dihydroisoquinoline
MS: calc.: $C_{22}H_{15}ClF_4N_2O_2S$ (482.89) f.: [M+1] 483.0 HPLC[min]: 6.77

3p. 1-[4-(2-Chloro-4-fluorobenzenesulfonamido)phenyl]-6-fluoro-3,4-dihydroisoquinoline
MS: calc.: $C_{21}H_{15}ClF_2N_2O_2S$ (432.88) f.: [M+1] 433.0 HPLC[min]: 5.29

3q. 1-[4-(4-n-Butyloxybenzenesulfonamido)phenyl]-6-fluoro-3,4-dihydroisoquinoline
MS: calc.: $C_{25}H_{25}FN_2O_3S$ (454.55) f.: [M+1] 453.1 HPLC[min]: 7.49

3r. 1-[4-(5-Dimethylaminonaphthalene-1-sulfonamido)phenyl]-6-fluoro-3,4-dihydroisoquinoline
MS: calc.: $C_{27}H_{24}FN_3O_2S$ (473.57) f.: [M+1] 474.2 HPLC[min]: 2.55

4a. 1-[4-(3,4-Difluorobenzenesulfonamido)phenyl]-7-fluoro-3,4-dihydroisoquinoline
MS: calc.: $C_{21}H_{15}F_3N_2O_2S$ (416.43) f.: [M+1] 417.1 HPLC[min]: 5.29

4b. 1-[4-(5-(Isoxazol-3-yl)thiophene-2-sulfonamido)phenyl]-7-fluoro-3,4-dihydroisoquinoline
MS: calc.: $C_{22}H_{16}FN_3O_3S_2$ (453.52) f.: [M+1] 454.0 HPLC[min]: 5.08

4c. 1-[4-(3-Trifluoromethylbenzenesulfonamido)phenyl]-7-fluoro-3,4-dihydroisoquinoline
MS: calc.: $C_{22}H_{16}F_4N_2O_2S$ (448.44) f.: [M+1] 449.0 HPLC[min]: 6.20

4d. 1-[4-(4-Benzenesulfonylthiophene-2-sulfonamido)phenyl]-7-fluoro-3,4-dihydroisoquinoline
MS: calc.: $C_{25}H_{19}FN_2O_4S_3$ (526.63) f.: [M+1] 527.1 HPLC[min]: 5.85

4e. 1-[4-(Naphthalene-2-sulfonamido)phenyl]-7-fluoro-3,4-dihydroisoquinoline
MS: calc.: $C_{25}H_{19}FN_2O_2S$ (430.5) f.: [M+1] 431.1 HPLC[min]: 6.13

4f. 1-[4-(4-Bromobenzenesulfonamido)phenyl]-7-fluoro-3,4-dihydroisoquinoline
MS: calc.: $C_{21}H_{16}BrFN_2O_2S$ (459.34) f.: [M+1] 459.0 HPLC[min]: 5.75

4g. 1-[4-(4-tert-Butylbenzenesulfonamido)phenyl]-7-fluoro-3,4-dihydroisoquinoline
MS: calc.: $C_{25}H_{25}FN_2O_2S$ (436.55) f.: [M+1] 437.2 HPLC[min]: 7.13

4h. 1-[4-(2-Phenylethenesulfonamido)phenyl]-7-fluoro-3,4-dihydroisoquinoline
MS: calc.: $C_{23}H_{19}FN_2O_2S$ (406.48) f.: [M+1] 407.1 HPLC[min]: 5.90

4i. 1-[4(4-Trifluoromethoxybenzenesulfonamido)phenyl]-7-fluoro-3,4-dihydroisoquinoline
MS: calc.: $C_{22}H_{16}F_4N_2O_3S$ (464.44) f.: [M+1] 465.1 HPLC[min]: 6.53

4k. 1-[4-(5-Chloro-3-methyl-benzo[b]thiophene-2-sulfonamido)phenyl]-7-fluoro-3,4-dihydroisoquinoline
MS: calc.: $C_{24}H_{18}ClFN_2O_2S_2$ (485.0) f.: [M+1] 485.1 HPLC[min]: 7.47

4l. 1-[4-(4-Methylbenzenesulfonamido)phenyl]-7-fluoro-3,4-dihydroisoquinoline
MS: calc.: $C_{22}H_{19}FN_2O_2S$ (394.47) f.: [M+1] 395.1 HPLC[min]: 5.13

4m. 1-[4-(2,5-Dimethoxybenzenesulfonamido)phenyl]-7-fluor-3,4-dihydroisoquinoline
MS: calc.: $C_{23}H_{21}FN_2O_4$ (440.50) f.: [M+1] 441.1 HPLC[min]: 4.73

4n. 1-[4-(4-Brom-2,5-dichlorothiophene-3-sulfonamido)phenyl]-7-fluoro-3,4-dihydrois oquinoline
MS: calc.: $C_{19}H_{12}BrCl_2FN_2O_2S_2$ (534.26) f.: [M+1] 534.9 HPLC[min]: 6.56

4o. 1-[4-(4-Bromo-5-chlorothiophene-2-sulfonamido)phenyl]-7-fluoro-3,4-dihydroisoquinoline
MS: calc.: $C_{19}H_{13}BrClFN_2O_2S_2$ (499.81) f.: [M+1] 501.0 HPLC[min]: 6.63

4p. 1-[4-(2-Methyl-3-chlorobenzenesulfonamido)phenyl]-7-fluoro-3,4-dihydroisoquinoline
MS: calc.: $C_{22}H_{18}ClFN_2O_2S$ (428.92) f.: [M+1] 429.0 HPLC[min]: 6.07

4q. 1-[4-(2-Trifluoromethoxybenzenesulfonamido)phenyl]-7-fluoro-3,4-dihydroisoquinoline
MS: calc.: $C_{22}H_{16}F_4N_2O_3S$ (464.44) f.: [M+1] 465.1 HPLC[min]: 6.01

4r. 1-[4-(2-Chloro-4-trifluoromethylbenzenesulfonamido)phenyl]-7-fluoro-3,4-dihydroisoquinoline
MS: calc.: $C_{22}H_{15}ClF_4N_2O_2S$ (482.89) f.: [M+1] 483.0 HPLC[min]: 6.65

4s. 1-[4-(2-Chloro-4-fluorobenzenesulfonamido)phenyl]-7-fluoro-3,4-dihydroisoquinoline
MS: calc.: $C_{21}H_{15}ClF_2N_2O_2S$ (432.88) f.: [M+1] 433.0 HPLC[min]: 5.16

4t. 1-[4-(4-n-Butyloxybenzenesulfonamido)phenyl]-7-fluoro-3,4-dihydroisoquinoline
MS: calc.: $C_{25}H_{25}FN_2O_3S$ (452.55) f.: [M+1] 453.1 HPLC[min]: 7.35

4u. 1-[4-(5-Dimethylaminonaphthalene-1-sulfonamido)phenyl]-7-fluoro-3,4-dihydroisoquinoline
MS: calc.: $C_{27}H_{24}FN_3O_2S$ (473.57) f.: [M+1] 474.1 HPLC[min]: 2.54

5a. 1-[4-(3-Trifluoromethylbenzenesulfonamido)-phenyl]-6-chloro-3,4-dihydroisoquinoline
MS: calc.: $C_{22}H_{16}ClF_3N_2O_2S$ (464.90) f.: [M+1] 465.1 HPLC[min]: 6.97

5b. 1-[4-(Naphthalene-2-sulfonamidophenyl]-6chloro-3,4-dihydroisoquinoline
MS: calc.: $C_{25}H_{19}ClN_2O_2S$ (446.96) f.: [M+1] 447.1 HPLC[min]: 6.87

5c. 1-[4-(4-tert-Butylbenzenesulfonamido)phenyl]-6-chloro-3,4-dihydroisoquinoline
MS: calc.: $C_{25}H_{25}ClN_2O_2S$ (453.01) f.: [M+1] 453.2 HPLC[min]: 7.99

5d. 1-[4-(2-Phenylethenesulfonamido)phenyl]-6-chloro-3,4-dihydroisoquinoline
MS: calc.: $C_{23}H_{19}ClN_2O_2S$ (422.94) f.: [M+1] 423.1 HPLC[min]: 6.44

5e. 1-[4-(4-Trifluoromethoxybenzenesulfonamido)phenyl]-6-chloro-3,4-dihydroisoquinoline
MS: calc.: $C_{22}H_{16}ClF_3N_2O_3S$ (480.90) f.: [M+1] 481.1 HPLC[min]: 7.29

5f. 1-[4-(2-Chloro-4-trifluoromethylbenzenesulfonamido)phenyl]-6-chloro-3,4-dihydroisoquinoline
MS: calc.: $C_{22}H_{15}Cl_2F_3N_2O_2S$ (499.34) f.: [M+1] 501.0 HPLC[min]: 7.39

5g. 1-[4-(2,6-Difluorobenzenesulfonamido)phenyl]-6-chloro-3,4-dihydroisoquinoline
MS: calc.: $C_{21}H_{15}ClF_2N_2O_2S$ (432.88) f.: [M+1] 433.1 HPLC[min]: 5.36

5h. 1-[4-(5-Dimethylaminonaphthalene-1-sulfonamido)phenyl]-6-chloro-3,4-dihydroisoquinoline
MS: calc.: $C_{27}H_{24}ClN_3O_2S$ (490.03) f.: [M+1] 490.1 HPLC[min]: 3.61

6a. 1-[4-(3,4-Difluorobenzenesulfonamido)phenyl]-7-chloro-3,4-dihydroisoquinoline
MS: calc.: $C_{21}H_{15}ClF_2N_2O_2S$ (432.88) f.: [M+1] 433.0 HPLC[min]: 5.97

6b. 1-[4-(5-(Isoxazol-3-yl)thiophene-2-sulfonamido)phenyl]-7-chloro-3,4-dihydroisoquinoline
MS: calc.: $C_{22}H_{16}ClN_3O_3S_2$ (469.97) f.: [M+1] 470.0 HPLC[min]: 5.67

6c. 1-[4-(3,5-Dimethylisoxazol-4-sulfnamid)phenyl]-7-chloro-3,4-dihydroisoquinoline
MS: calc.: $C_{20}H_{18}ClN_3O_3S$ (415.90) f.: [M+1] 416.0 HPLC[min]: 4.73

6d. 1-[4-(3-Trifluor methylbenzenesulf namido)phenyl]-7-chlor-3,4-dihydroisoquinoline
MS: calc.: $C_{22}H_{16}ClF_3N_2O_2S$ (464.90) f.: [M+1] 465.1 HPLC[min]: 6.75

6e. 1-[4-(Naphthalene-2-sulfonamido)phenyl]-7-chloro-3,4-dihydroisoquinoline
MS: calc.: $C_{25}H_{19}ClN_2O_2S$ (446.96) f.: [M+1] 447.1 HPLC[min]: 6.65

6f. 1-[4-(4-Bromobenzenesulfonamido)phenyl]-7-chloro-3,4-dihydroisoquinoline
MS: calc.: $C_{21}H_{16}BrClN_2O_2S$ (475.79) f.: [M+1] 477.0 HPLC[min]: 6.35

6g. 1-[4-(4-tert-Butylbenzenesulfonamido)phenyl]-7-chloro-3,4-dihydroisoquinoline
MS: calc.: $C_{25}H_{25}ClN_2O_2S$ (453.01) f.: [M+1] 453.1 HPLC[min]: 7.77

6h. 1-[4-(2-Phenylethenesulfonamido)phenyl]-7-chloro-3,4-dihydroisoquinoline
MS: calc.: $C_{23}H_{19}ClN_2O_2S$ (422.94) f.: [M+1] 423.1 HPLC[min]: 6.21

6i. 1-[4-(4-Trifluoromethoxybenzenesulfonamido)phenyl]-7-chloro-3,4-dihydroisoquinoline
MS: calc.: $C_{22}H_{16}ClF_3N_2O_3S$ (480.9) f.: [M+1] 481.0 HPLC[min]: 7.07

6k. 1-[4-(5-Chloro-3-methylbenzo[b]thiophene-2-sulfonamido)phenyl]-7-chloro-3,4-dihydroisoquinoline
MS: calc.: $C_{24}H_{18}Cl_2N_2O_2S_2$ (501.46) f.: [M+1] 503.0 HPLC[min]: 8.05

6l. 1-[4-(2,5-Dimethoxybenzenesulfonamido)phenyl]-7-chloro-3,4-dihydroisoquinoline
MS: calc.: $C_{23}H_{21}ClN_2O_4S$ (456.95) f.: [M+1] 457.1 HPLC[min]: 5.39

6m. 1-[4-(4-Bromo-5chlorothiophene-2-sulfonamido)phenyl]-7-chloro-3,4-dihydroisoquinoline
MS: calc.: $C_{19}H_{13}BrCl_2N_2O_2S_2$ (516.27) f.: [M+1] 517.0 HPLC[min]: 7.25

6n. 1-[4-(2-Methyl-3-chlorobenzenesulfonamido)phenyl]-7-chlor-3,4-dihydroisoquinoline
MS: calc.: $C_{22}H_{18}Cl_2N_2O_2S$ (445.37) f.: [M+1] 445.0 HPLC[min]: 6.69

6o. 1-[4-(2-Chl ro-4-trifluoromethylbenzenesulf namido)phenyl]-7-chloro-3,4-dihydroisoquinoline
MS: calc.: $C_{22}H_{15}Cl_2F_3N_2O_2S$ (499.34) f.: [M+1] 499.0 HPLC[min]: 7.22

6p. 1-[4-(2-Chloro-4-fluorobenzenesulfonamido)phenyl]-7-chloro-3,4-dihydroisoquinoline
MS: calc.: $C_{21}H_{15}Cl_2FN_2O_2S$ (449.33) f.: [M+1] 449.0 HPLC[min]: 5.88

6q. 1-[4-(2,6-Difluorobenzenesulfonamido)phenyl]-7-chloro-3,4-dihydroisoquinoline
MS: calc.: $C_{21}H_{15}ClF_2N_2O_2S$ (432.88) f.: [M+1] 433.0 HPLC[min]: 5.19

6r. 1-[4-(5-Dimethylaminonaphthalene-1-sulfonamido)phenyl]-7-chloro-3,4-dihydroisoquinoline
MS: calc.: $C_{27}H_{24}ClN_3O_2S$ (490.03) f.: [M+1] 490.2 HPLC[min]: 7.75

7a. 1-[4-(3,4-Difluorobenzenesulfonamido)phenyl]-6-trifluoromethyl-3,4-dihydroisoquinoline
MS: calc.: $C_{22}H_{15}F_5N_2O_2S$ (466.43) f.: [M+1] 467.1 HPLC[min]: 6.80

7b. 1-[4-(5-(Isoxazol-3-yl)thiophene-2-sulfonamido)phenyl]-6-trifluoromethyl-3,4-dihydroisoquinoline
MS: calc.: $C_{23}H_{16}F_3N_3O_3S_2$ (503.53) f.: [M+1] 504.1 HPLC[min]: 6.59

7c. 1-[4-(3,5-Dimethylisoxazole-4-sulfonamido)phenyl]-6-trifluoromethyl-3,4-dihydroisoquinoline
MS: calc.: $C_{21}H_{18}F_3N_3O_3S$ (449.46) f.: [M+1] 450.1 HPLC[min]: 5.83

7d. 1-[4-(3-Trifluoromethylbenzenesulfonamido)phenyl]-6-trifluoromethyl-3,4-dihydroisoquinoline
MS: calc.: $C_{23}H_{16}F_6N_2O_2S$ (498.45) f.: [M+1] 499.1 HPLC[min]: 7.61

7e. 1-[4-(4-Benzenesulf nylthiophene-2-sulfonamido)phenyl]-6-trifluoromethyl-3,4-dihydroisoquinoline
MS: calc.: $C_{26}H_{19}F_3N_2O_4S_3$ (576.64) f.: [M+1] 577.1 HPLC[min]: 7.29

7f. 1-[4-(Naphthalene-2-sulfonamido)phenyl]-6-trifluoromethyl-3,4-dihydroisoquinoline
MS: calc.: $C_{26}H_{19}F_3N_2O_2S$ (480.51) f.: [M+1] 481.1 HPLC[min]: 7.53

7g. 1-[4-(4-Bromobenzenesulfonamido)phenyl]-6-trifluoromethyl-3,4-dihydroisoquinoline
MS: calc.: $C_{22}H_{16}BrF_3N_2O_2S$ (509.35) f.: [M+1] 509.1 HPLC[min]: 7.19

7h. 1-[4-(4-tert-Butylbenzenesulfonamido)phenyl]-6-trifluoromethyl-3,4-dihydroisoquinoline
MS: calc.: $C_{26}H_{25}F_3N_2O_2S$ (486.56) f.: [M+1] 487.1 HPLC[min]: 8.85

7i. 1-[4-(4-Trifluoromethoxybenzenesulfonamido)phenyl]-6-trifluoromethyl-3,4-dihydroisoquinoline
MS: calc.: $C_{23}H_{16}F_6N_2O_3S$ (514.45) f.: [M+1] 515.1 HPLC[min]: 8.01

7k. 1-[4-(5-Chloro-3-methyl-benzo[b]thiophene-2-sulfonamido)phenyl]-6-trifluoromethyl-3,4-dihydroisoquinoline
MS: calc.: $C_{25}H_{18}ClF_3N_2O_2S_2$ (535.01) f.: [M+1] 535.1 HPLC[min]: 9.23

7l. 1-[4-(4-Bromo-2,5-dichlorothiophene-3-sulfonamido)phenyl]-6-trifluoromethyl-3,4-dihydroisoquinoline
MS: calc.: $C_{20}H_{21}BrCl_2F_3N_2O_2S_2$ (584.26) f.: [M+1] 584.9 HPLC[min]: 8.06

7m. 1-[4-(4-Bromo-5-chlorothiophene-2-sulfonamido)phenyl]-6-trifluoromethyl-3,4-dihydroisoquinoline
MS: calc.: $C_{20}H_{13}BrClF_3N_2O_2S_2$ (549.82) f.: [M+1] 550.9 HPLC[min]: 8.14

7n. 1-[4-(2-Methyl-3-chlorobenzenesulfonamido)phenyl]-6-trifluoromethyl-3,4-dihydroisoquinolin
MS: calc.: $C_{23}H_{18}ClF_3N_2O_2S$ (478.92) f.: [M+1] 479.0 HPLC[min]: 7.47

7. 1-[4-(2-Trifluor methoxybenzenesulfonamido)phenyl]-6-trifluoromethyl-3,4-dihydroisoquinoline
MS: calc.: $C_{23}H_{16}F_6N_2O_3S$ (514.45) f.: [M+1] 515.1 HPLC[min]: 7.42

7p. 1-[4-(2-Chloro-4-trifluoromethylbenzenesulfonamido)phenyl]-6-trifluoromethyl-3,4-dihydroisoquinoline
MS: calc.: $C_{23}H_{15}ClF_6N_2O_2S$ (532.90) f.: [M+1] 533.0 HPLC[min]: 8.13

7q. 1-[4-(2-Chloro-4-fluorobenzenesulfonamido)phenyl]-6-trifluoromethyl-3,4-dihydroisoquinoline
MS: calc.: $C_{22}H_{15}ClF_4N_2O_2S$ (482.89) f.: [M+1] 483.0 HPLC[min]: 6.75

7r. 1-[4-(5-Dimethylaminonaphthalene-1-sulfonamido)phenyl]-6-trifluoromethyl-3,4-dihydroisoquinoline
MS: calc.: $C_{28}H_{24}F_3N_3O_2S$ (523.58) f.: [M+1] 524.2 HPLC[min]: 4.85

8a. 1-[4-(5-(Isoxazol-3-yl)thiophene-2-sulfonamido)phenyl]-7-phenoxy-3,4-dihydroisoquinoline
MS: calc.: $C_{28}H_{21}N_3O_4S_2$ (527.63) f.: [M+1] 528.0 HPLC[min]: 7.28

8b. 1-[4-(3-Trifluoromethylbenzenesulfonamido)phenyl]-7-phenoxy-3,4-dihydroisoquinoline
MS: calc.: $C_{28}H_{21}F_3N_2O_3S$ (522.55) f.: [M+1] 523.0 HPLC[min]: 7.57

8c. 1-[4-(4-Benzenesulfonylthiophene-2-sulfonamido)phenyl]-7-phenoxy-3,4-dihydroisoquinoline
MS: calc.: $C_{31}H_{24}N_2O_5S_3$ (600.74) f.: [M+1] 601.0 HPLC[min]: 7.44

8d. 1-[4-(Naphthalene-2-sulfonamido)phenyl]-7-phenoxy-3,4-dihydroisoquinoline

MS: calc.: $C_{31}H_{24}N_2O_3S$ (504.61) f.: [M+1] 505.1 HPLC [min]: 7.55

8e. 1-[4-(4-Methylbenzenesulfonamido)phenyl]-7-phenoxy-3,4-dihydroisoquinoline
MS: calc.: $C_{28}H_{24}N_2O_3S$ (468.58) f.: [M+1] 469.0 HPLC [min]: 7.33

8f. 1-[4-(4-Trifluoromethoxybenzenesulfonamido)phenyl]-7-phenoxy-3,4-dihydroisoquinoline
MS: calc.: $C_{28}H_{21}F_3N_2O_4S$ (538.55) f.: [M+1] 539.0 HPLC[min]: 7.65

9a. 1-[4-(3,4-Difluorobenzenesulfonamido)phenyl]-3,4-dihydroisoquinoline
MS: calc.: $C_{21}H_{16}F_2N_2O_2S$ (398.43) f.: [M+1] 399.1 HPLC[min]: 5.10

9b. 1-[4-(5-(Isoxazol-3-yl)thiophene-2-sulfonamido)phenyl]-3,4-dihydroisoquinoline
MS: calc.: $C_{22}H_{17}N_3O_3S_2$ (435.53) f.: [M+1] 436.1 HPLC[min]: 4.85

9c. 1-[4-(3,5-Dimethylisoxazole-4-sulfonamido)phenyl]-3,4-dihydroisoquinoline
MS: calc.: $C_{20}H_{19}N_3O_3S$ (381.46) f.: [M+1] 382.1 HPLC [min]: 3.51

9d. 1-[4-(3-Trifluoromethylbenzenesulfonamido)phenyl]-3,4-dihydroisoquinoline
MS: calc.: $C_{22}H_{17}F_3N_2O_2S$ (430.45) f.: [M+1] 431.1 HPLC[min]: 6.03

9e. 1-[4-(4-Benzenesulfonylthiophene-2-sulfonamido)phenyl]-3,4-dihydroisoquinoline
MS: calc.: $C_{25}H_{20}N_2O_4S_3$ (508.64) f.: [M+1] 509.1 HPLC[min]: 5.68

9f. 1-[4-(Naphthalene-2-sulfonamido)phenyl]-3,4-dihydroisoquinoline
MS: calc.: $C_{25}H_{20}N_2O_2S$ (412.51) f.: [M+1] 413.1 HPLC [min]: 5.91

9g. 1-[4-(4-tert-Butylbenzenesulfonamido)phenyl]-3,4-dihydroisoquinoline
MS: calc.: $C_{25}H_{26}N_2O_2S$ (418.56) f.: [M+1] 419.1 HPLC [min]: 7.01

9h. 1-[4-(4-Trifluoromethoxybenzenesulfonamido)phenyl]-3,4-dihydroisoquinoline
MS: calc.: $C_{22}H_{17}F_3N_2O_3S$ (446.45) f.: [M+1] 447.1 HPLC[min]: 6.38

9i. 1-[4-(6-Chloroimidazo[2,1-b]thiazole-5-sulfonamido)phenyl]-3,4-dihydroisoquinoline
MS: calc.: $C_{20}H_{15}ClN_4O_2S_2$ (442.95) f.: [M+1] 443.0 HPLC[min]: 8.16

9k. 1-[4-(5-Chloro-3-methyl-benzo[b]thiophene-2-sulfonamido)phenyl]-3,4-dihydroisoquinoline
MS: calc.: $C_{24}H_{19}ClN_2O_2S_2$ (467.01) f.: (M+1] 467.1 HPLC[min]: 7.37

9l. 1-[4-(2,5-Dimethoxybenzenesulfonamido)phenyl]-3,4-dihydroisoquinoline
MS: calc.: $C_{23}H_{22}N_2O_4S$ (422.51) f.: [M+1] 423.1 HPLC [min]: 4.40

9m. 1-[4-(4-Bromo-2,5-dichlorothiophene-3-sulfonamido)phenyl]-3,4-dihydroisoquinoline
MS: calc.: $C_{19}H_{13}BrCl_2N_2O_2S_2$ (516.27) f.: [M+1] 516.9 HPLC[min]: 6.46

9n. 1-[4-(4-Bromo-5-chlorothiophene-2-sulfonamido)phenyl]-3,4-dihydroisoquinoline
MS: calc.: $C_{19}H_{14}BrClN_2O_2S_2$ (481.82) f.: [M+1] 482.9 HPLC[min]: 6.49

9o. 1-[4-(2-Methyl-3-chlorobenzenesulfonamido)phenyl]-3,4dihydroisoquinoline
MS: calc.: $C_{22}H_{19}ClN_2O_2S$ (410.93) f.: [M+1] 411.1 HPLC[min]: 5.95

9p. 1-[4-(2-Trifluoromethoxybenzenesulfonamido)phenyl]-3,4-dihydroisoquinoline
MS: calc.: $C_{22}H_{17}F_3N_2O_3S$ (446.45) f.: [M+1] 447.1 HPLC[min]: 5.85

9q. 1-[4-(2-Chloro-4-trifluoromethylbenzenesulfonamido)phenyl]-3,4-dihydroisoquinoline
MS: calc.: $C_{22}H_{16}ClF_3N_2O_2S$ (464.9) f.: [M+1] 465.1 HPLC[min]: 6.49

9r. 1-[4-(2-Chloro-4-fluorobenzenesulfonamido)phenyl]-3,4-dihydroisoquinoline
MS: calc.: $C_{21}H_{16}ClFN_2O_2S$ (414.89) f.: [M+1] 415.1 HPLC[min]: 4.95

9s. 1-[4-(2,6-Difluorobenzenesulfonamido)phenyl]-3,4-dihydroisoquinoline
MS: calc.: $C_{21}H_{16}F_2N_2O_2S$ (398.43) f.: [M+1] 399.1 HPLC[min]: 4.08

9t. 1-[4-(5-Dimethylaminonaphthalene-1-sulfonamido)phenyl]-3,4-dihydroisoquinoline
MS: calc.: $C_{27}H_{25}N_3O_2S$ (455.58) f.: [M+1] 456.2 HPLC [min]: 2.16

10a. 1-[3-(3,4-Difluorobenzenesulfonamido)phenyl]-6-fluoro-3,4-dihydroisoquinoline
MS: calc.: $C_{21}H_{15}F_3N_2O_2S$ (416.43) f.: [M+1] 417.1 HPLC[min]: 5.17

10b. 1-[3-(5-(Isoxazol-3-yl)-thiophene-2-sulfonamido)pheny]-6-fluoro-3,4-dihydroisoquinoline
MS: calc.: $C_{22}H_{16}FN_3O_3S_2$ (453.52) f.: [M+1] 454.1 HPLC[min]: 4.70

10c. 1-[3-(3.5-Dimethylisoxazole-4-sulfonamido)phenyl]-6-fluoro-3,4-dihydroisoquinoline
MS: calc.: $C_{20}H_{18}FN_3O_3S$ (399.45) f.: [M+1] 400.1 HPLC[min]: 3.56

10d. 1-[3-(3-Trifluoromethylbenzenesulfonamido)phenyl]-6-fluoro-3,4-dihydroisoquinoline
MS: calc.: $C_{22}H_{16}F_4N_2O_2S$ (448.44) f.: [M+1] 449.1 HPLC[min]: 6.08

10e. 1-[3-(Naphthalene-2-sulfonamido)phenyl]-6-fluoro-3,4-dihydroisoquinoline
MS: calc.: $C_{25}H_{19}FN_2O_2S$ (430.5) f.: [M+1] 431.1 HPLC [min]: 5.91

10f. 1-[3-(4-Bromobenzenesulfonamido)phenyl]-6-fluoro-3,4-dihydroisoquinoline
MS: calc.: $C_{21}H_{16}BrFN_2O_2S$ (459.43) f.: [M+1] 459.0 HPLC[min]: 5.60

10g. 1-[3-(4-tert-Butylbenzenesulfonamido)phenyl]-6-fluoro-3,4-dihydroisoquinoline
MS: calc.: $C_{25}H_{25}FN_2O_2S$ (436.55) f.: [M+1] 437.1 HPLC[min]: 7.05

10h. 1-[3-(2-Phenylethenesulfonamido)phenyl]-6-fluoro-3,4-dihydroisoquinoline
MS: calc.: $C_{23}H_{19}FN_2O_2S$ (406.48) f.: [M+1] 407.1 HPLC[min]: 5.41

10i. 1-[4-(4-Trifluoromethoxybenzenesulfonamido)phenyl]-6-fluoro-3,4-dihydroisoquinoline
MS: calc.: $C_{22}H_{16}F_4N_2O_3S$ (464.44) f.: [M+1] 465.1 HPLC[min]: 6.43

10k. 1-[4-(5-Chloro-3-methylbenz[b]thiophene-2-sulfonamido)phenyl]-6-fluoro-3,4-dihydroisoquinolin
MS: calc.: $C_{24}H_{18}ClFN_2O_2S_2$ (485.0) f.: [M+1] 485.1 HPLC[min]: 7.28

10l. 1-[3-(2,5-Dimethoxybenzenesulfonamido)phenyl]-6-fluoro-3,4-dihydroisoquinoline
MS: calc.: $C_{23}H_{21}FN_2O_4S$ (440.50) f.: [M+1] 441.0 HPLC[min]: 4.27

10m. 1-[3-(4-Bromo-2,5-dichlorothiophene-3-sulfonamido)phenyl]-6-fluoro-3,4-dihydroisoquinoline
MS: calc.: $C_{19}H_{12}BrCl_2FN_2O_2S_2$ (534.26) f.: [M+1] 534.9 HPLC[min]: 6.41

10n. 1-[3-(4-Bromo-5-chlorothiophene-2-sulfonamido)phenyl]-6-fluoro-3,4-dihydroisoquinoline MS: calc.: $C_{19}H_{13}BrClFN_2O_2S_2$ (499.81) f.: [M+1] 500.9 HPLC[min]: 6.52

10o. 1-[3-(2-Methyl-3-chlorobenzenesulfonamido)phenyl]-6-fluoro-3,4-dihydroisoquinoline
MS: calc.: $C_{22}H_{18}ClFN_2O_2S$ (428.92) f.: [M+1] 429.1 HPLC[min]: 5.91

10p. 1-[3-(2-Trifluoromethoxybenzenesulfonamido)phenyl]-6-fluoro-3,4-dihydroisoquinoline
MS: calc.: $C_{22}H_{16}F_4N_2O_3S$ (464.44) f: [M+1] 465.1 HPLC[min]: 5.80

10q. 1-[3-(2-Chloro-4-trifluoromethylbenzenesulfonamido)phenyl]-6-fluoro-3,4-dihydroisoquinoline
MS: calc.: $C_{22}H_{15}ClF_4N_2O_2S$ (482.89) f.: [M+1] 483.1 HPLC[min]: 6.53

10r. 1-[3-(2-Chloro-4-fluorobenzenesulfonamidophenyl]-6-fluoro-3,4-dihydroisoquinoline
MS: calc.: $C_{21}H_{15}ClF_2N_2O_2S$ (432.88) f.: [M+1] 433.0 HPLC[min]: 5.01

10s. 1-[3-(2,5-Difluorobenzenesulfonamido)phenyl]-6-fluoro-3,4-dihydroisoquinoline
MS: calc.: $C_{21}H_{15}F_3N_2O_2S$ (416.43) f.: [M+1] 417.1 HPLC[min]: 3.99

10t. 1-[3-(5-Dimethylamin naphthalene-1-sulfonamido)phenyl]-6-fluoro-3,4-dihydroisoquinoline
MS: calc.: $C_{27}H_{24}FN_3O_2S$ (473.57) f.: [M+1] 474.1 HPLC[min]: 2.05

11a. 1-[3-(3.5-Dimethylisoxazol-4-sulfonamido)phenyl]-7-fluoro-3,4-dihydroisoquinoline
MS: calc.: $C_{20}H_{18}FN_3O_3S$ (399.45) f.: [M+1] 400.1 HPLC[min]: 3.53

11b. 1-[3-(3-Trifluoromethylbenzenesulfonamido)phenyl]-7-fluoro-3,4-dihydroisoquinoline
MS: calc.: $C_{22}H_{16}F_4N_2O_2S$ (448.44) f.: [M+1] 449.1 HPLC[min]: 5.97

11c. 1-[3-(4-Benzenesulfonylthiophene-2-sulfonamido)phenyl]-7-fluoro-3,4-dihydroisoquinoline
MS: calc.: $C_{25}H_{19}FN_2O_4S_3$ (526.63) f.: [M+1] 527.0 HPLC[min]: 5.55

11d. 1-[3-(Naphthalene-2-sulfonamido)phenyl]-7-fluoro-3,4-dihydroisoquinoline
MS: calc.: $C_{25}H_{19}FN_2O_2S$ (430.5) f.: [M+1] 431.1 HPLC[min]: 5.81

11e. 1-[3-(4-tert-Butylbenzenesulfonamido)phenyl]-7-fluoro-3,4-dihydroisoquinoline
MS: calc.: $C_{25}H_{25}FN_2O_2S$ (436.55) f.: [M+1] 437.1 HPLC[min]: 7.05

11f. 1-[4-(2-Phenylethenesulfonamido)phenyl]-7-fluoro-3,4-dihydroisoquinoline
MS: calc.: $C_{23}H_{19}FN_2O_2S$ (406.48) f.: [M+1] 407.1 HPLC[min]: 5.33

11g. 1-[3-(4-Trifluoromethoxybenzenesulfonamido)phenyl]-7-fluoro-3,4-dihydroisoquinoline
MS: calc.: $C_{22}H_{16}F_4N_2O_3S$ (464.44) f.: [M+1] 465.1 HPLC[min]: 6.37

11h. 1-[3-(5-Chloro-3-methylbenzo[b]thiophene-2-sulfonamido)phenyl]-7-fluoro-3,4-dihydroisoquinoline
MS: calc.: $C_{24}H_{18}ClFN_2O_2S_2$ (485.0) f.: [M+1] 485.1 HPLC[min]: 7.17

11i. 1-[3-(Isopropylsulfonamido)phenyl]-7-fluoro-3,4-dihydroisoquinoline
MS: calc.: $C_{18}H_{19}FN_2O_2S$ (346.43) f.: [M+1] 347.1 HPLC[min]: 2.39

11k. 1-[3-(2,5-Dimethoxybenzenesulfonamido)phenyl]-7-fluoro-3,4-dihydroisoquinoline
MS: calc.: $C_{23}H_{21}FN_2O_4$ (440.50) f.: [M+1] 441.0 HPLC[min]: 4.31

11l. 1-[3-(4-Bromo-2,5-dichlorothiophene-3-sulfonamido)phenyl]-7-fluoro-3,4-dihydroisoquinoline
MS: calc.: $C_{19}H_{12}BrCl_2FN_2O_2S_2$ (534.26) f.: [M+1] 534.9 HPLC[min]: 6.36

11m. 1-[3-(4-Bromo-5-chlorothiophene-2-sulfonamido)phenyl]-7-fluoro-3,4-dihydroisoquinoline
MS: calc.: $C_{19}H_{13}BrClFN_2O_2S_2$ (499.81) f.: [M+1] 500.9 HPLC[min]: 6.42

11n. 1-[3-(2-Methyl-3-chlorobenzenesulfonamido)phenyl]-7-fluoro-3,4-dihydroisoquinoline
MS: calc.: $C_{22}H_{18}ClFN_2O_2S$ (428.92) f.: [M+1] 429.0 HPLC[min]: 5.87

11o. 1-[3-(2-Trifluoromethoxybenzenesulfonamido)phenyl]-7-fluoro-3,4-dihydrosoquinoline
MS: calc.: $C_{22}H_{16}F_4N_2O_3S$ (464.44) f.: [M+1] 465.1 HPLC[min]: 5.68

11p. 1-[3-(2-Chloro-4-trifluoromethylbenzenesulfonamido)phenyl]-7-fluoro-3,4-dihydroisoquinoline
MS: calc.: $C_{22}H_{15}ClF_4N_2O_2S$ (482.89) f.: [M+1] 483.1 HPLC[min]: 6.42

11q. 1-[3-(2-Chloro-4-fluorobenzenesulfonamido)phenyl]-7-fluoro-3,4-dihydroisoquinoline
MS: calc.: $C_{21}H_{15}ClF_2N_2O_2S$ (432.88) f.: [M+1] 433.1 HPLC[min]: 4.95

11r. 1-[3-(2,5-Difluorobenzenesulfonamido)phenyl]-7-fluoro-3,4-dihydroisoquinoline
MS: calc.: $C_{21}H_{15}F_3N_2O_2S$ (416.43) f.: [M+1] 417.1 HPLC[min]: 3.95

12a. 1-[3-(3,4-Difluorobenzenesulfonamido)phenyl]-6-chloro-3,4-dihydroisoquinoline
MS: calc.: $C_{21}H_{15}ClF_2N_2O_2S$ (432.88) f.: [M+1] 433.1 HPLC[min]: 6.00

12b. 1-[3-(5-(Isoxazol-3-yl)-thiophene-2-sulfonamido)phenyl]-6-chloro-3,4-dihydroisoquinoline
MS: calc.: $C_{22}H_{16}ClN_3O_3S_2$ (469.97) f.: [M+1] 470.0 HPLC[min]: 5.59

12c. 1-[3-(3,5-Dimethylisoxazole-4-sulfonamido)phenyl]-6-chloro-3,4-dihydroisoquinoline
MS: calc.: $C_{20}H_{18}ClN_3O_3S$ (415.90) f.: [M+1] 416.1 HPLC[min]: 4.75

12d. 1-[3-(3-Trifluoromethylbenzenesulfonamido)phenyl]-6-chloro-3,4-dihydroisoquinoline
MS: calc.: $C_{22}H_{16}ClF_3N_2O_2S$ (464.90) f.: [M+1] 465.1 HPLC[min]: 6.75

12e. 1-[3-(4-Benzenesulfonylthiophene-2-sulfonamido)phenyl]-6-chloro-3,4-dihydroisoquinoline
MS: calc.: $C_{25}H_{19}ClN_2O_4S_3$ (543.09) f.: [M+1] 543.01 HPLC[min]: 6.64

12f. 1-[4-(Naphthalene-2-sulfonamido)phenyl]-6-chloro-3,4-dihydroisoquinoline
MS: calc.: $C_{25}H_{19}ClN_2O_2S$ (446.96) f.: [M+1] 447.1 HPLC[min]: 6.54

12g. 1-[3-(4-Bromobenzenesulfonamido)phenyl]-6-chloro-3,4-dihydroisoquinoline
MS: calc.: $C_{21}H_{16}BrClN_2O_2S$ (475.79) f.: [M+1] 476.9 HPLC[min]: 6.34

12h. 1-[3-(4-Cyanobenzenesulfonamido)phenyl]-6-chloro-3,4-dihydroisoquinoline
MS: calc.: $C_{22}H_{16}ClN_3O_2S$ (421.91) f.: [M+1] 422.0 HPLC[min]: 5.05

12i. 1-[3-(4-tert-Butylbenzenesulfonamido)phenyl]-6-chloro-3,4-dihydroisoquinoline
MS: calc.: $C_{25}H_{25}ClN_2O_2S$ (453.01) f.: [M+1] 453.1 HPLC[min]: 7.75

12k. 1-[3-(2-Phenylethenesulfonamid)phenyl]-6-chloro-3,4-dihydr isoquinoline
MS: calc.: $C_{23}H_{19}ClN_2O_2S$ (???) f.: [M+1] ??? HPLC [min]: 6.15

12l. 1-[3-(4-Trifluoromethoxybenzenesulf namido)phenyl]-6-chloro-3,4-dihydroisoquinoline MS: calc.: $C_{22}H_{16}ClF_3N_2O_3S$ (480.90) f.: [M+1] 481.0 HPLC[min]: 7.07

12m. 1-[3-(3-Methoxy-4-methoxycarbonylthiophene-2-sulfonamido)phenyl]-6-chloro-3,4-dihydroisoquinoline
MS: calc.: $C_{22}H_{19}ClN_2O_5S_2$ (490.99) f.: [M+1] 491.0 HPLC[min]: 5.43

12n. 1-[3-(5-Chloro-3-methyl-benzo[b]thiophene-2-sulfonamido)phenyl]-6-chloro-3,4-dihydroisoquinoline
MS: calc.: $C_{24}H_{18}Cl_2N_2O_2S_2$ (501.46) f.: [M+1] 501.1 HPLC[min]: 7.96

12o. 1-[3-(4-Methylbenzenesulfonamido)phenyl]-6-chloro-3,4-dihydroisoquinoline
MS: calc.: $C_{22}H_{19}ClN_2O_2S$ (410.93) f.: [M+1] 411.1 HPLC[min]: 5.75

12p. 1-[3-(2,5-Dimethoxybenzenesulfonamido)phenyl]-6-chloro-3,4-dihydroisoquinoline
MS: calc.: $C_{23}H_{21}ClN_2O_4S$ (456.95) f.: [M+1] 457.1 HPLC[min]: 5.25

12q. 1-[3-(4-Bromo-2,5-dichlorothiophene-3-sulfonamido)phenyl]-6-chloro-3,4-dihydroisoquinoline
MS: calc.: $C_{19}H_{12}BrCl_3N_2O_2S_2$ (550.71) f.: [M+1] 550.8 HPLC[min]: 7.08

12r. 1-[3-(4-Bromo-5-chlorothiophene-2-sulfonamido)phenyl]-6-chloro-3,4-dihydroisoquinoline
MS: calc.: $C_{19}H_{13}BrCl_2N_2O_2S_2$ (516.27) f.: [M+1] 516.9 HPLC[min]: 7.12

12s. 1-[3-(2-Methyl-3-chlorobenzenesulfonamido)phenyl]-6-chloro-3,4-dihydroisoquinoline
MS: calc.: $C_{22}H_{18}Cl_2N_2O_2S$ (445.37) f.: [M+1] 445.0 HPLC[min]: 6.62

12t. 1-[3-(2-Chloro-4-trifluoromethylbenzenesulfonamido)phenyl]-6-chloro-3,4-dihydroisoquinoline
MS: calc.: $C_{22}H_{15}Cl_2F_3N_2O_2S$ (499.34) f.: [M+1] 499.0 HPLC[min]: 7.23

12u. 1-[3-(2-Chloro-4-fluorobenzenesulfonamido)phenyl]-6-chloro-3,4-dihydroisoquinoline
MS: calc.: $C_{21}H_{15}Cl_2FN_2O_2S$ (449.33) f.: [M+1] 449.0 HPLC[min]: 5.85

12v. 1-[3-(4-Butyloxybenzenesulfonamido)phenyl]-6chloro-3,4dihydroisoquinoline
MS: calc.: $C_{25}H_{25}ClN_2O_3S$ (469.01) f.: [M+1] 469.1 HPLC[min]: 7.90

12w. 1-[3-(2,5-Difluorobenzenesulfonamido)phenyl)-6-chloro-3,4-dihydroisoquinoline
MS: calc.: $C_{21}H_{15}ClF_2N_2O_2S$ (432.88) f.: [M+1] 433.0 HPLC[min]: 5.05

13a. 1-[3-(3,4-Difluorobenzenesulfonamido)phenyl]-7-chloro-3,4-dihydroisoquinoline
MS: calc.: $C_{21}H_{15}ClF_2N_2O_2S$ (432.88) f.: [M+1] 433.0 HPLC[min]: 5.80

13b. 1-[3-(5-(Isoxazol-3-yl)thiophene-2-sulfonamido)phenyl]-7-chloro-3,4-dihydroisoquinoline
MS: calc.: $C_{22}H_{16}ClN_3O_3S_2$ (469.97) f.: [M+1] 470.1 HPLC[min]: 5.37

13c. 1-[3-(3,5-Dimethylisoxazole-4-sulfonamido)phenyl]-7-chloro-3,4-dihydroisoquinoline
MS: calc.: $C_{20}H_{18}ClN_3O_3S$ (415.90) f.: [M+1] 416.0 HPLC[min]: 4.51

13d. 1-[4-(3-Trifluoromethylbenzenesulfonamido phenyl]-7-chloro-3,4-dihydroisoquinoline
MS: calc.: $C_{22}H_{16}ClF_3N_2O_2S$ (464.90) f.: [M+1] 465.1 HPLC[min]: 6.55

13e. 1-[3-(4-Benzenesulfonylthiophene-2-sulfonamido)phenyl]-7-chloro-3,4-dihydroisoquinoline
MS: calc.: $C_{25}H_{19}ClN_2O_4S_3$ (543.09) f.: [M+1] 543.1 HPLC[min]: 6.11

13f. 1-[3-(Naphthalene-2-sulfonamido)phenyl]-7-chloro-3,4-dihydroisoquinoline
MS: calc.: $C_{25}H_{19}ClN_2O_2S$ (446.96) f.: [M+1] 447.1 HPLC[min]: 6.43

13g. 1-[3-(4-Bromobenzenesulfonamido)phenyl]-7-chloro-3,4-dihydroisoquinoline
MS: calc.: $C_{21}H_{16}BrClN_2O_2S$ (475.79) f.: [M+1] 477.0 HPLC[min]: 6.19

13h. 1-[3-(4-Cyan benzenesulfonamido)phenyl]-7-chloro-3,4-dihydroisoquinoline
MS: calc.: $C_{22}H_{16}ClN_3O_2S$ (421.91) f.: [M+1] 422.0 HPLC[min]: 4.76

13i. 1-[3-(4-tert-Butylbenzenesulfonamido)phenyl]-7-chloro-3,4-dihydroisoquinoline
MS: calc.: $C_{25}H_{25}ClN_2O_2S$ (453.01) f.: [M+1] 453.2 HPLC[min]: 7.53

13k. 1-[3-(2-Phenylethenesulfonamido)phenyl]-7-chloro-3,4-dihydroisoquinoline
MS: calc.: $C_{23}H_{19}ClN_2O_2S$ (422.94) f.: [M+1] 423.1 HPLC[min]: 5.97

13l. 1-[3-(4-Trifluoromethoxybenzenesulfonamido)phenyl]-7-chloro-3,4-dihydroisoquinoline
MS: calc.: $C_{22}H_{16}ClF_3N_2O_3S$ (480.9) f.: [M+1] 481.0 HPLC[min]: 6.89

13m. 1-[3-(3-Methoxy-4-methoxycarbonylthiophene-2-sulfonamido)phenyl]-7-chloro-3,4-dihydroisoquinoline
MS: calc.: $C_{22}H_{19}ClN_2O_5S_2$ (490.99) f.: [M+1] 491.0 HPLC[min]: 5.21

13n. 1-[3-(5-Chloro-3-methylbenzo[b]thiophene-2-sulfonamido)phenyl]-7-chloro-3,4-dihydroisoquinoline
MS: calc.: $C_{24}H_{18}Cl_2N_2O_2S_2$ (501.46) f.: [M+1] 501.0 HPLC[min]: 7.79

13o. 1-[3-(4-Methylbenzenesulfonamido)phenyl]-7-chloro-3,4-dihydroisoquinoline
MS: calc.: $C_{22}H_{19}ClN_2O_2S$ (410.93) f.: [M+1] 411.1 HPLC[min]: 5.59

13p. 1-[3-(2,5-Dimethoxybenzenesulfonamido)phenyl]-7-chloro-3,4-dihydroisoquinoline
MS: calc.: $C_{23}H_{21}ClN_2O_4S$ (456.95) f.: [M+1] 457.1 HPLC[min]: 4.98

13q. 1-[3-(4-Bromo-2,5-dichlorothiophene-3-sulfonamido)phenyl]-7-chloro-3,4-dihydroisoquinoline
MS: calc.: $C_{19}H_{12}BrCl_3N_2O_2S_2$ (550.71) f.: [M+1] 550.9 HPLC[min]: 6.95

13r. 1-[3-(4-Bromo-5-chlorothi phene-2-sulfonamido)phenyl]-7-chloro-3,4-dihydroisoquinoline
MS: calc.: $C_{19}H_{13}BrCl_2N_2O_2S_2$ (516.27) f.: [M+1] 516.9 HPLC[min]: 7.06

13s. 1-[3-(2-Methyl-3-chlorobenzenesulfonamido)phenyl]-7-chloro-3,4-dihydroisoquinoline
MS: calc.: $C_{22}H_{18}Cl_2N_2O_2S$ (445.37) f.: [M+1] 445.0 HPLC[min]: 6.50

13t. 1-[3-(2-Trifluoromethoxybenzenesulfonamido)phenyl]-7-chloro-3,4-dihydroisoquinoline
MS: calc.: $C_{22}H_{16}ClF_3N_2O_3S$ (480.90) f.: [M+1] 481.0 HPLC[min]: 6.33

13u. 1-[3-(2-Chloro-4-trifluoromethylbenzenesulfonamido)phenyl]-7-chloro-3,4-dihydroisoquinoline
MS: calc.: $C_{22}H_{15}Cl_2F_3N_2O_2S$ (499.34) f.: [M+1] 499.0 HPLC[min]: 7.05

13v. 1-[3-(2-Chloro-4-fluorobenzenesulfonamido)phenyl]-7-chloro-3,4-dihydroisoquinoline
MS: calc.: $C_{21}H_{15}Cl_2FN_2O_2S$ (449.33) f.: [M+1] 449.0 HPLC[min]: 5.68

13w. 1-[3-(4-Butyloxybenzenesulfonamido)phenyl]-7-chloro-3,4-dihydroisoquinoline
MS: calc.: $C_{25}H_{25}ClN_2O_3S$ (469.01) f.: [M+1] 469.0 HPLC[min]: 7.71

13x. 1-[3-(2,6-Difluorobenzenesulfonamido)phenyl]-7-chloro-3,4-dihydroisoquinoline MS: calc.: $C_{21}H_{15}ClF_2N_2O_2S$ (432.88) f.: [M+1] 433.0 HPLC[min]: 4.83

13y. 1-[3-(5-Dimethylaminonaphthalene-1-sulfonamido)phenyl]-7-chloro-3,4-dihydroisoquinoline
MS: calc.: $C_{27}H_{24}ClN_3O_2S$ (490.03) f.: [M+1] 490.1 HPLC[min]: 2.97

14a. 1-[3-(3,4-Difluorobenzenesulfonamido)phenyl]-6-trifluoromethyl-3,4-dihydroisoquinoline
MS: calc.: $C_{22}H_{15}F_5N_2O_2S$ (466.43) f.: [M+1] 467.1 HPLC[min]: 6.61

14b. 1-[3-(5-(Isoxazol-3-yl)thiophene-2-sulfonamido)phenyl]-6-trifluoromethyl-3,4-dihydroisoquinoline
MS: calc.: $C_{23}H_{16}F_3N_3O_3S_2$ (503.53) f.: [M+1] 504.1 HPLC[min]: 6.26

14c. 1-[4-(3,5-Dimethylisoxazol-4-sulfonamido)phenyl]-6-trifluoromethyl-3,4-dihydroisoquinoline
MS: calc.: $C_{21}H_{18}F_3N_3O_3S$ (449.46) f.: [M+1] 450.0 HPLC[min]: 5.59

14d. 1-[3-(3-Trifluoromethylbenzenesulfonamido)phenyl]-6-trifluoromethyl-3,4-dihydroisoquinoline
MS: calc.: $C_{23}H_{16}F_6N_2O_2S$ (498.45) f.: [M+1] 499.0 HPLC[min]: 7.33

14e. 1-[3-(Naphthalene-2-sulfonamido)phenyl]-6-trifluoromethyl-3,4-dihydroisoquinoline
MS: calc.: $C_{26}H_{19}F_3N_2O_2S$ (480.51) f.: [M+1] 481.1 HPLC[min]: 7.13

14f. 1-[3-(4-Bromobenzenesulfonamido)phenyl]-6-trifluoromethyl-3,4-dihydroisoquinoline
MS: calc.: $C_{22}H_{16}BrF_3N_2O_2S$ (509.35) f.: [M+1] 509.0 HPLC[min]: 6.94

14g. 1-[3-(4-Cyanobenzenesulfonamido)phenyl]-6-trifluoromethyl-3,4-dihydroisoquinoline
MS: calc.: $C_{23}H_{16}F_3N_3O_2S$ (455.46) f.: [M+1] 456.0 HPLC[min]: 5.85

14h. 1-[3-(4-tert-Butylbenzenesulfonamido)phenyl]-6-trifluoromethyl-3,4-dihydroisoquinoline
MS: calc.: $C_{26}H_{25}F_3N_2O_2S$ (486.56) f.: [M+1] 487.1 HPLC[min]: 8.56

14i. 1-[3-(2-Phenylethensulfonamido)phenyl]-6-trifluoromethyl-3,4-dihydroisoquinoline
MS: calc.: $C_{24}H_{19}F_3N_2O_2S$ (456.49) f.: [M+1] 457.1 HPLC[min]: 6.77

14k. 1-[3-(4-Trifluoromethoxybenzenesulfonamido)phenyl]-6-trifluoromethyl-3,4-dihydroisoquinoline
MS: calc.: $C_{23}H_{16}F_6N_2O_3S$ (514.45) f.: [M+1] 515.0 HPLC[min]: 7.70

14l. 1-[3-(5-Chl ro-3-methyl-benzo[b]thiophene-2-sulfonamido)phenyl]-6-trifluoromethyl-3,4-dihydroisoquinoline
MS: calc.: $C_{25}H_{18}ClF_3N_2O_2S_2$ (535.01) f.: [M+1] 535.1 HPLC[min]: 8.65

14m. 1-[3-(4-Methylbenzenesulfonamido)phenyl]-6-trifluoromethyl-3,4-dihydroisoquinoline
MS: calc.: $C_{23}H_{19}F_3N_2O_2S$ (444.48) f.: [M+1] 445.1 HPLC[min]: 6.42

14n. 1-[3–4-Bromo-5-chlorothiophene-2-sulfonamido)phenyl]-6-trifluoromethyl-3,4-dihydroisoquinoline
MS: calc.: $C_{20}H_{13}BrClF_3N_2O_2S_2$ (549.82) f.: [M+1] 550.9 HPLC[min]: 7.80

14o. 1-[3-(2-Methyl-3-chlorobenzenesulfonamido)phenyl]-6-trifluoromethyl-3,4-dihydroisoquinoline
MS: calc.: $C_{23}H_{18}ClF_3N_2O_2S$ (478.92) f.: [M+1] 479.0 HPLC[min]: 7.23

14p. 1-[3-(2-Trifluoromethoxybenzenesulfonamido)phenyl]-6-trifluoromethyl-3,4-dihydroisoquinoline
MS: calc.:$C_{23}H_{16}F_6N_2O_3S$ (514.45) f.: [M+1] 515.1 HPLC[min]: 7.13

14q. 1-[3-(2-Chloro-4-trifluoromethylbenzenesulfonamido)phenyl]-6-trifluoromethyl-3,4-dihydroisoquinoline
MS: calc.: $C_{23}H_{15}ClF_6N_2O_2S$ (532.90) f.: [M+1] 533.0 HPLC[min]: 7.85

14r. 1-[4-(2-Chloro-4-fluorobenzenesulfonamido)phenyl]-6-trifluoromethyl-3,4-dihydroisoquinoline
MS: calc.: $C_{22}H_{15}ClF_4N_2O_2S$ (482.89) f.: [M+1] 483.0 HPLC[min]: 6.55

14s. 1-[3-(4-Butyloxybenzenesulfonamido)phenyl]-6-trifluoromethyl-3,4-dihydroisoquinoline
MS: calc.: $C_{26}H_{25}F_3N_2O_3S$ (502.56) f.: [M+1] 503.1 HPLC[min]: 8.66

14t. 1-[3-(2,5-Diflu r benzenesulfonamid)phenyl]-6-trifluoromethyl-3,4-dihydr isoquinoline
MS: calc.: $C_{22}H_{15}F_5N_2O_2S$ (466.43) f.: [M+1] 467.1 HPLC[min]: 5.85

15a. 1-[3-(5-(Isoxazol-3-yl)thiophene-2-sulfonamid)phenyl]-3,4-dihydroisoquinoline
MS: calc.: $C_{22}H_{17}N_3O_3S_2$ (435.53) f.: [M+1] 436.1 HPLC[min]: 4.52

15b. 1-[3-(3.5-Dimethylisoxazol-4-sulfonamido)phenyl]-3,4-dihydroisoquinoline
MS: calc.: $C_{20}H_{19}N_3O_3S$ (381.46) f.: [M+1] 382.1 HPLC[min]: 3.25

15c. 1-[3-(3-Trifluoromethylbenzenesulfonamido)phenyl]-3,4-dihydroisoquinoline
MS: calc.: $C_{22}H_{17}F_3N_2O_2S$ (430.45) f.: [M+1] 431.1 HPLC[min]: 5.85

15d. 1-[3-(Naphthalene-2-sulfonamido)phenyl]-3,4-dihydroisoquinoline
MS: calc.: $C_{25}H_{20}N_2O_2S$ (412.51) f.: [M+1] 413.1 HPLC[min]: 5.65

15e. 1-[3-(4-tert-Butylbenzenesulfonamido)phenyl]-3,4-dihydroisoquinoline
MS: calc.: $C_{25}H_{26}N_2O_2S$ (418.56) f.: [M+1] 419.1 HPLC[min]: 6.87

15f. 1-[3-(2-Phenylethensulfonamido)phenyl]-3,4-dihydroisoquinoline
MS: calc.: C23H20N2O2S (388.49) f.: [M+1] 389.1 HPLC[min]: 5.15

15g. 1-[3-(4-Trifluoromethoxybenzenesulfonamido)phenyl]-3,4-dihydroisoquinoline
MS: calc.: $C_{22}H_{17}F_3N_2O_3S$ (446.45) f.: [M+1] 447.1 HPLC[min]: 6.25

15h. 1-[3-(6-Chloroimidazo[2,1-b]thiazol-5-sulfonamido)phenyl]-3,4-dihydroisoquinoline
MS: calc.: $C_{20}H_{15}ClN_4O_2S_2$ (442.95) f.: [M+1] 443.1 HPLC[min]: 7.95

15i. 1-[3-(5-Chloro-3-methylbenzo[b]thiophene-2-sulfonamido)phenyl]-3,4-dihydroisoquinoline
MS: calc.: $C_{24}H_{19}ClN_2O_2S_2$ (467.01) f.: [M+1] 467.1 HPLC[min]: 7.11

15k. 1-[3-(4-Br m-5-chlorothiophene-2-sulfonamido)phenyl]-3,4-dihydroisoquinoline
MS: calc.: $C_{19}H_{14}BrClN_2O_2S_2$ (481.82) f.: [M+1] 482.9 HPLC[min]: 6.35

15l. 1-[3-(2-Methyl-3-chlorobenzenesulfonamido)phenyl]-3,4-dihydroisoquinoline
MS: calc.: $C_{22}H_{19}ClN_2O_2S$ (410.93) f.: [M+1] 411.1 HPLC[min]: 5.70

15m. 1-[3-(2-Trifluoromethoxybenzenesulfonamido)phenyl]-3,4-dihydrosoquinoline
MS: calc.: $C_{22}H_{17}F_3N_2O_3S$ (446.45) f.: [M+1] 447.1 HPLC[min]: 5.59

15n. 1-[3-(2-Chloro-4-trifluoromethylbenzenesulfonamido)phenyl]-3,4-dihydroisoquinoline
MS: calc.: $C_{22}H_{16}ClF_3N_2O_2S$ (464.9) f.: [M+1] 465.1 HPLC[min]: 6.37

15o. 1-[3-(2-Chloro-4-fluorobenzenesulfonamido)phenyl]-3,4-dihydroisoquinoline
MS: calc.: $C_{21}H_{16}ClFN_2O_2S$ (414.89) f.: [M+1] 415.0 HPLC[min]:4.75

15p. 1-[3-(2,6-Difluorobenzenesulfonamido)phenyl]-3,4-dihydroisoquinoline
MS: calc.: $C_{21}H_{16}F_2N_2O_2S$ (398.43) f.: [M+1] 399.0 HPLC[min]: 3.69

15q. 1-[3-(5-Dimethylaminonaphthalene-1-sulfonamido)phenyl]-3,4-dihydroisoquinoline
MS: calc.: $C_{27}H_{25}N_3O_2S$ (455.58) f.: [M+1] 456.3 HPLC [min]: 1.99

16a. 1-[4-(4-Trifluoromethoxybenzenesulfonamido)-3-methoxyphenyl]-7-chloro-isoquinoline
500 mg of 1-[4-(4-Trifluoromethoxybenzenesulfonamido)-3-methoxyphenyl]-7-chloro-3,4-dihydroisoquinoline (1a) are dissolved in 500 μl of of dimethylformamide. To this solution 560 mg of potassium tert.-butylate in 4000 μl of dimethylformamide are added under an atmosphere of oxygen. The reaction mixture is stirred at RT for 4 h and evaporated to dryness. The residue is dissolved in ethyl acetate/water and the organic layer is separated. The aqueous layer is extracted twice with ethyl acetate and the combined organic layers are dried and evaporated. The product is stirred out of diethylether to yield 215 mg of the title compound.
MS: calc.: $C_{23}H_{16}ClF_3N_2O_4S$ (508.91) f.: [M+1] 509.1
$^1$H NMR (200 MHz, $D_6$-DMSO): δ=3.52 (s,3H), 7.18–7.22 (m,2H), 7.43 (d,J=8.5 Hz,1H), 7.56–7.60 (m,2H), 7.80–7.93 (m,6H), 8.12 (d,J=8.8 Hz,1H), 8.60 (d,J=5.8 Hz,1H), 9.90 (s,1H).

16b. 1-[4-(4-Trifluor methoxybenzenesulfonamido)-3-hydroxyphenyl]-7-chloro-isoquinoline
150 mg of 1-[4-(4-Trifluoromethoxybenzenesulfonamido)-3-methoxyphenyl]-7-chloroisoquinoline are dissolved in 3 ml of dichloromethane and cooled to –40° C. 2.95 ml of 1M boron tribromide solution in dichloromethane are added and the reaction mixture is allowed to warm to RT and stirred for 16 h. It is diluted with dichloromethane and isopropanol and the pH is adjusted to 7. The organic layer is separated and the aqueous layer is extracted twice. The organic layers are combined and evaporated. The residue is purified by flash chromatography on silica gel.
MS: calc.: $C_{22}H_{14}ClF_3N_2O_4S$ (494.88) f.: [M+1] 495.1
$^1$H NMR (200 MHz, $D_6$-DMSO): δ=7.02–7.07 (m,2H), 7.34 (d,J=8.6 Hz,1H), 7.54–7.59 (m,2H), 7.79–7.97 (m,5H), 8.10 (d, J=8.8 Hz,1H), 8.57 (d,J=5.6 Hz,1H).

17a. 1-[4-(4-Trifluoromethoxybenzenesulfonamido)-3-methoxyphenyl]-5-fluoro-3,4-dihydroisoquinoline
The title compound is obtained in accordance with the procedure described in Example 1a.
MS: calc.: $C_{23}H_{18}F_4N_2O_4S$ (494.47) f.: [M+1] 495.2
$^1$H NMR (200 MHz, $D_6$-DMSO): δ=2.67–2.75 (m,2H), 3.69–3.76 (s,3H), 3.77 (m,2H), 6.99–7.08 (m,3H), 7.30–7.38 (m,3H), 7.54–7.58 (m,2H), 7.82–7.89 (m,2H), 9.83 (s, 1H).

17b. 1-4-(4-Trifluoromethoxybenzenesulfonamido)-3-hydroxyphenyl]-5-fluoro-3,4-dihydroisoquinoline
The title compound is obtained in accordance with the procedure described in Example 16b.
MS: calc.: $C_{22}H_{16}F_4N_2O_4S$ (480.44) f.: [M+1] 481.1
$^1$H NMR (200 MHz, $D_6$-DMSO): δ=2.67–2.73 (m,2H), 3.67–3.74 (m,2H), 6.87-6.97 (m,3H), 7.22–7.37 (m,3H), 7.52–7.56 (m,2H), 7.88–7.92 (m,2H).

18a. 1-[4-(4-Trifluoromethoxybenzenesulfonamido)-3-hydroxyphenyl]-7chloro-3,4-dihydroisoquinoline
The title compound is obtained in accordance with the procedure described in Example 16b.
MS calc.: $C_{22}H_{16}ClF_3N_2O_4S$ (496.90) f.: [M+1] 497.1 HPLC[min]: 6.93

18b. 1-[4-(Naphthalene-2-sulfonamido)-3-hydroxyphenyl]-7chloro-3,4-dihydroisoquinoline
The title compound is obtained in accordance with the procedure described in Example 16b.
MS: calc.: $C_{25}H_{19}ClN_2O_3S$ (462.96) f.: [M+1] 463.2 HPLC[min]: 6.77

19. 4-(7-Chloro-3,4-dihydro-isoquinolin-1-yl)-N-(4-trifluoromethoxy-phenyl)-benzenesulfonamide
The title compound is obtained in accordance with the procedure described in Example 1a with using 4-(7-chloro-3,4-dihydro-isoquinoline-1-yl)-benzenesulfonyl chloride and 4-trifluoromethoxyphenylamine as starting materials.
MS: calc.: $C_{22}H_{16}ClF_3N_2O_3S$ (480.90) f.: [M+1] 481.2
$^1$H NMR (200 MHz, $D_6$-DMSO): δ=2.69–2.76 (m,2H), 3.72–3.79 (m,2H), 6.99 (d,J=2.0 Hz,1H), 7.17–7.29 (m,4H), 7.27 (d,J=9.3 Hz,1H), 7.53 (dd,J=8.2 Hz,J=1.9 Hz,1H), 7.2 (d,J=8.5 Hz,2H), 7.85 (d,J=8.5 Hz,2H).

Starting Compounds

A1. 1-(4-Amino-3-methoxyphenyl)-7-chloro-3,4-dihydroisoquinoline
3 g of 1-(3-methoxy4-nitrophenyl)-7chloro-3,4-dihydroisoquinoline (starting compound B1) are suspended in methanol, and 2.4 g of ammonium formate and 60 mg of palladium on charcoal (10%) are added to this suspension. The reaction mixture is stirred at RT for 5 h, filtered through Celite and concentrated. The residue is purified by flash chromatography on silica gel. It is stirred out of diethyl ether/n-hexane, filtered with suction and dried. 2.4 g of the title compound are obtained.
$^1$H-NMR (200 MHz. $D_6$-DMSO): δ=2.67 (m,2H), 3.64 (m,2H), 3.79 (s,3H), 5.13 (s,2H), 6.66 (d,J=8.0 Hz,1H), 6.88 (dd,J=8.0 Hz,J=1.8 Hz,1H), 7.09 (d,J=1.8 Hz,1H), 7.26 (d,J=2.2 Hz,1H), 7.38 (d,J=8.0 Hz,1H), 7.49 (dd,J=8.0 Hz, J=2.2 Hz,1H).

The following compounds are obtained in accordance with this procedure:

A2. 1-(4-Amino-3-methoxyphenyl)-3,4-dihydroisoquinoline
$^1$H NMR (200 MHz, $D_6$-DMSO): δ=2.67 (m,2H), 3.62 (m,2H), 3.78 (s,3H), 5.06 (s, 2H), 6.64 (d,J=8.0Hz,1H), 6.89 (dd,J=8.0 Hz,J=1.8 Hz,H), 7.10 (d,J=1.8 Hz,H), 7.29–7.45 (m,4H).

A3. 1-(4-Aminophenyl)-6-fluoro-3,4-dihydroisoquinoline
$^1$H NMR (200 MHz, $D_6$-DMSO): δ=2.68 (m,2H), 3.59 (m,2H), 5.43 (s,2H), 6.57 (m,1H), 6.61 (m,1H), 7.05–7.47 (m,5H).

A4. 1-(4-Aminophenyl)-7-fluoro-3,4-dihydroisoquinoline
$^1$H NMR (200 MHz, $D_6$-DMSO): δ=2.64 (m,2H), 3.63 (m,2H), 5.47 (s,2H), 6.60 (m,1H), 6.64 (m,1H), 7.00 (dd, J=9.7 Hz,=2.6 Hz,1H), 7.26–7.42 (m,4H).

A5. 1-(4-Aminophenyl)-6-chloro-3,4-dihydroisoquinoline
$^1$H NMR (200 MHz, $D_6$-DMSO): δ=2.67 (m,2H), 3.61 (m, 2H), 5.44 (s,2H), 6.59 (d,J=8.5 Hz,2H), 7.25–7.42 (m,5H).

A6. 1-(4-Aminophenyl)-7-chloro-3,4-dihydroisoquinoline
$^1$H NMR (200 MHz, $D_6$-DMSO): δ=2.65 (m,2H), 3.62 (m,2H), 5.47 (s,2H), 6.63 (d,J=8.6 Hz,2H), 7.22–7.38 (m,4H), 7.47 (dd,J=8.0 Hz,J=2.1 Hz,1H).

A7. 1-(4-Aminophenyl)-6-trifluoromethoxy-3,4-dihydroisoquinoline
$^1$H NMR (200 MHz, $D_6$-DMSO): δ=2.77 (m,2H), 3.66 (m,2H), 5.47 (s,2H), 6.57 (m,1H), 6.62 (m,1H), 7.27 (m,1H), 7.31 (m,1H), 7.48 (d,J=8.0 Hz,1H), 7.65 (s,1H), 7.71 (m,1H).

A8. 1-(4-Aminophenyl)-7-phenoxy-3,4-dihydroisoquinoline $^1$H NMR (200 MHz, D$_6$-DMSO): δ=2.65 (m,2H), 3.63 (m,2H), 5.41 (s,2H), 6.54 (d,J=8.5 Hz,2H), 6.88 (d,J=2.5 Hz,1H), 6.99 (m,1H), 7.03 (m,1H), 7.07–7.13 (m,2H), 7.24–7.40 (m,5H).

A9. 1-(4-Aminophenyl)-3,4-dihydroisoquinoline $^1$H NMR (200 MHz, D$_6$-DMSO): δ=2.66 (m,2H), 3.60 (m,2H), 5.41 (s,2H), 6.57 (m,1H), 6.62 (m,1H), 7.25–7.44 (m,6H).

A10. 1-(3-Aminophenyl)-6-fluoro-3,4-dihydroisoquinoline $^1$H NMR (200 MHz, D$_6$-DMSO): δ=2.72 (m,2H), 3.66 (m,2H), 5.16 (s,2H), 6.59–6.67 (m,2H), 6.75 (m,1H), 6.97–7.29 (m,4H).

A11. 1-(3-Aminophenyl)-7-fluoro-3,4-dihydroisoquinoline $^1$H NMR (200 MHz, D$_6$-DMSO): δ=2.68 (m,2H), 3.69 (m,2H), 5.18 (s,2H), 6.63–6.68 (m,2H), 6.77 (m,1H), 6.92 (dd,J=9.6 Hz,J=2.6 Hz,1H), 7.09 (t,J=7.8 Hz,1H), 7.23–7.43 (m,2H).

A12. 1-(3-Aminophenyl)-6-chloro-3,4-dihydroisoquinoline $^1$H NMR (200 MHz, D$_6$-DMSO): δ=2.72 (m,2H), 3.67 (m,2H), 5.16 (s,2H), 6.60–6.67 (m,2H), 6.75 (m,1H), 7.07 (m,1H), 7.20 (d,J=8.2 Hz,1H), 7.36 (dd,J=8.2 Hz,J=2.2 Hz,1H), 7.44 (d,J=2.0 Hz,1H).

A13. 1-(3-Aminophenyl)-7-chloro-3,4-dihydroisoquinoline hydrochloride $^1$H NMR (200 MHz, D$_6$-DMSO): δ=3.21 (m,2H), 3.98 (m,2H), 7.35–7.37 (m,2H), 7.39–7.49 (m,2H), 7.59 (d,J=7.7 Hz,1H), 7.66 (d,J=8.1 Hz,1H), 7.90 (dd,J=8.1 Hz,J=2.2 Hz,1H).

A14. 1-(3-Aminophenyl)-6-trifluoromethoxy-3,4-dihydroisoquinoline

Thin layer chromatography (silica gel: ether acetate/petroleum ether (low boiling): 2/1) R$_f$=0.2; m.p. 131–136° C.

A15. 1-(3-Aminophenyl)-3,4-dihydroisoquinoline $^1$H NMR (200 MHz, D$_6$-DMSO): δ=2.70 (m,2H), 3.67 (m,2H), 5.16 (s,2H), 6.63 (m,1H), 6.66 (m,1H), 6.78 (m,1H), 7.11 (m,1H), 7.19–7.68 (m,4H).

A16. 1-(4-Amino-3-methoxyphenyl)-5-fluoro-3,4-dihydroisoquinoline $^1$H NMR (200 MHz, D$_6$-DMSO): δ=2.64–2.70 (m,2H), 3.61–3.68 (m,2H), 3.77 (s,3H), 5.09 (s,2H), 6.64 (d,J=8.0 Hz,1H), 6.88 (dd,J=8.0 Hz,J=1.8 Hz,1H), 7.09 (d,J=1.8 Hz,1H), 7.17–7.24 (m,1H), 7.27–7.37 (m,2H).

B1. 1-(3-Methoxy-4-nitrophenyl)-7-chloro-3,4-dihydroisoquinoline 6.9 g of 2-(4-chlorophenyl)ethylamine and 10.8 g of 3-methoxy-4-nitrobenzoic acid are dissolved in 400 ml of dichloromethane. 10.5 g of N-dimethylaminoethyl-N'-ethylcarbodiimide are added and the mixture is stirred at RT for 16 h. It is then extracted with in each case 250 ml of 1N hydrochloric acid, saturated sodium hydrogen carbonate solution and water, and the organic phase is dried over magnesium sulfate. It is concentrated and the residue is stirred out of diethyl ether/N-hexane, filtered off with suction and dried.

The resulting amide is suspended in 300 ml of absolute toluene, after which 19 g of phosphorus pentoxide are added and the mixture is heated to boiling. After 4 h, a further 19 g of phosphorus pentoxide are added and the reaction mixture is kept at boiling temperature for a further 16 h. It is cooled down, after which 300 ml of water are carefully added and the mixture is brought to pH 11 with 40% sodium hydroxide solution. The organic phase is separated off and the aqueous phase is extracted a further 3 times with 150 ml of ethyl acetate; the combined organic extracts are then dried over magnesium sulfate. They are then concentrated and the residue purified by flash chromatography on silica gel. The product is stirred out of isopropanoldiethyl ether, filtered off with suction and dried. 11.35 g of the title compound are obtained.

$^1$H NMR (200 MHz, D$_6$-DMSO): δ=2.77 (m,2H), 3.80 (m,2H), 3.96 (s,3H), 7.16 (d,J=2.1 Hz,1H), 7.22 (dd,J=8.3 Hz,J=1.5 Hz,1H), 7.43 (d,J=8.1 Hz1H), 7.48 (d,J=1.5 Hz,1H), 7.55 (dd,J=8.1 Hz,J=2.1 Hz,1H), 7.97 (d,J=8.3 Hz,1H).

The following are obtained in accordance with this procedure:

B2. 1-(3-Meth xy-4-nitr phenyl)-3,4-dihydroisoquinoline

The title compound was directly subjected to further processing without any physical data being collected.

B3. 1-(4-Nitrophenyl)-6-fluor-3,4-dihydroisoquinoline $^1$H NMR (200 MHz, D$_6$-DMSO): δ=2.80 (m,2H), 3.79 (m,2H), 7.12–7.20 (m,2H), 7.29 (dd,J=9.1 Hz,J=2.2 Hz,1H), 7.78 (m,1H), 7.81 (m,1H), 8.28 (m,1H), 8.33 (m,1H).

B4. 1-(4-Nitrophenyl)-7-fluoro-3,4-dihydroisoquinoline $^1$H NMR (200 MHz, D$_6$-DMSO): δ=2.76 (m,2H), 3.82 (m,2H), 6.91 (dd,J=9.4 Hz,J=2.4 Hz,1H), 7.29–7.49 (m,2H), 7.80 (m,1H), 7.84 (m,1H), 8.29 (m,1H), 8.34 (m,1H).

B5. 1-(4-Nitrophenyl)-6-chloro-3,4-dihydroisoquinoline hydrochloride $^1$H NMR (200 MHz, D$_6$-DMSO): δ=3.20 (m,2H), 4.01 (m,2H), 7.33 (d,J=8.1 Hz,1H), 7.54 (dd,J=8.4 Hz,J=2.1 Hz,1H), 7.76 (d,J=2.1 Hz,1H), 7.98 (m,1H), 8.02 (m,1H), 8.45 (m,1H), 8.49 (m,1H).

B6. 1-(4-Nitrophenyl)-7-chloro-3,4-dihydroisoquinoline $^1$H NMR (200 MHz, D$_6$-DMSO): δ=2.77 (m,2H), 3.82 (m,2H), 7.09 (d,J=2.1 Hz,1H), 7.44 (d,J=8.1 Hz,1H), 7.56 (dd,J=8.1 Hz,J=2.1 Hz,1H), 7.79 (m,1H), 7.85 (m,1H), 8.30 (m,1H) 8.35 (m,1H).

B7. 1-(4-Nitrophenyl)-6-trifluoromethyl-3,4-dihydroisoquinoline

Thin layer chromatography (silica gel: ethyl acetate/petroleum ether (low boiling); 2/1) R$_f$=0.4;

B8. 1-(4-Nitrophenyl)-7-phenoxy-3,4-dihydroisoquinoline $^1$H NMR (200 MHz, D$_6$-DMSO): δ=2.76 (m,2H), 3.83 (m,2H), 6.76 (d,J=2.5 Hz,1H), 7.01 (m,1H), 7.06 (m,1H), 7.10–7.17 (m,2H), 7.32–7.45 (m,3H), 7.78 (m,1H), 7.82 (m,1H), 8.07 (m,1H), 8.25 (m,1H).

B9. 1-(4-Nitrophenyl)-3,4-dihydroisoquinoline $^1$H NMR (200 MHz, D$_6$-DMSO): δ=2.78 (m,2H), 3.80 (m,2H), 7.13 (d,J=7.7 Hz,1H), 7.28–7.52 (m,3H), 7.78 (m,1H), 7.82 (m,1H), 8.28 (m,1H), 8.32 (m,1H).

B10. 1-(3-Nitrophenyl)-6-fluoro-3,4-dihydroisoquinoline $^1$H NMR (200 MHz, D$_6$-DMSO): δ=2.80 (m,2H), 3.78 (m,2H), 7.08–7.31 (m,3H), 7.72 (m,1H), 8.0 (m,1H), 8.32–8.37 (m,2H).

B11. 1-(3-Nitrophenyl)-7-fluoro-3,4-dihydroisoquinoline $^1$H NMR (200 MHz, D$_6$-DMSO): δ=2.76 (m,2H), 3.81 (m,2H), 6.98 (dd,J=9.4 Hz,J=2.6 Hz,1H), 7.29–7.49 (m,2H), 7.77 (m,1H), 8.01 (dd,J=6.4 Hz,J=1.4 Hz,1H), 8.27–8.38 (m,2H).

B12. 1-(3-Nitrophenyl)-6-chloro-3,4-dihydroisoquinoline $^1$H NMR (200 MHz, D$_6$-DMSO): δ=3.19 (m,2H), 4.0 (m,2H), 7.39 (d,J=8.5 Hz,1H), 7.54 (dd,J=8.5 Hz,J=2.1 Hz,1H), 7.75 (d,J=2.1 Hz,1H), 7.94 (m,1H), 8.15 (m,1H), 8.54–8.60 (m,2H).

B13. 1-(3-Nitrophenyl)-7-chloro-3,4-dihydroisoquinoline $^1$H NMR (200 MHz, D$_6$-DMSO): δ=2.78 (m,2H), 3.80 (m,2H), 7.15 (d,J=2.1 Hz,1H), 7.45 (d,J=8.1 Hz,1H), 7.47 (dd,J=8.1 Hz,J=2.1 Hz,1H), 7.78 (m,1H), 8.0 (m,1H), 8.33–8.38 (m,2H).

B14. 1-(3-Nitrophenyl)-6-trifluoromethoxy-3,4-dihydroisoquinoline $^1$H NMR (200 MHz, D$_6$-DMSO): δ=2.89 (m,2H), 3.85 (m,2H), 7.22 (m,1H), 7.45 (m,1H), 7.67–7.82 (m,2H), 8.02 (m,1H), 8.33–8.40 (m,2H).

B15. 1-(3-Nitrophenyl)-3,4-dihydroisoquinoline $^1$H NMR (200 MHz, D$_6$-DMSO): δ=2.78 (m,2H), 3.80 (m,2H), 7.18 (m,1H), 7.26-7.53 (M,3H), 7.76 (m,1H), 8.00 (m,1H), 8.31–8.37 (m,2H).

B16. 1-(4-Nitro-3-methoxyphenyl)-5-fluoro-3,4-dihydroisoquinoline $^1$H NMR (200 MHz, D$_6$-DMSO): δ=2.73–2.81 (m,2H), 3.79–3.86 (m,2H), 3.94 (s,3H), 7.0–7.13 (m,1H), 7.21 (dd, J=8.3 Hz,J=1.6 Hz,1H), 7.28–7.52 (m,3H), 7.96 (d,J=8.3 Hz,1H).

Industrial Applicability

Of the 11 phosphodiesterase (PDE) isoenzymes which are presently known, PDE7 was described for the first time, as HCP1 ("high affinity cAMP-specific PDE"), in 1993 (Michaeli T, Bloom T J, Martins T, Loughney K, Ferguson K, Riggs M, Rodgers L, Beavo J A and Wigler M, Isolation and characterization of a previously undetected human cAMP phosphodiesterase by complementation of cAMP phosphosterase-deficient *Saccharomyces cerevisiae*, J Biol Chem 268: 12925–12932, 1993). According to today's nomenclature, HCP1 is human PDE7A1; in addition to this, another human splicing variant of the same gene (PDE7A2) (Han P, Zhu X and Michaeli T, Alternative splicing of the high affinity cAMP-specific phosphodiesterase (PDE7A) mRNA in human skeletal muscle and heart. J Biol Chem 272: 16152–16157, 1997) and a second human PDE7 gene (PDE7B) (Sasaki T, Kotera J, Yuasa K and Omori K, Identification of human PDE7B, a cAMP-specific phosphodiesterase. Biochem Biophys Res Commun 271: 575–583, 2000) were described in the subsequent years. Individual representatives of the PDE7 isoenzyme are characterized by being particularly prominently expressed in specific areas of the brain (putamen, caudate nucleus), in skeletal muscle, in leukemic T cell lines and in native CD4+ T cells. The induction of PDE7 has been described as being an essential prerequisite for activating T cells (Li L, Yee C and Beavo J A, CD3- and CD28-dependent induction of PDE7 required for T cell activation. Science 283: 848–851, 1999).

The compounds according to the invention therefore possess valuable pharmacological properties, which make them utilizable in industry, and can be employed as therapeutic agents for the treatment and prophylaxis of diseases in human and veterinary medicine. As selective cyclic nucleotide phosphodiesterase (PDE) inhibitors (specifically of type 7 PDE), they are preferably suitable for treating T cell-mediated diseases of an inflammatory nature, for example of the airways (bronchial asthma, COPD), of the skin (dermatoses such as psoriasis and atopic dermatitis), of the kidney (glomerulonephritis), of the pancreas (autoimmune diabetes), of the central nervous system (multiple sclerosis), of the intestine (Crohn's disease, ulcerative colitis), of the eyes (conjunctivitis) and of the joints (rheumatoid arthritis), and, furthermore, for suppressing the T cell activity which is responsible for the rejection of transplanted organs, such as the kidney, the liver, the lung and the heart, and for inhibiting the degenerate proliferation of T cells in various forms of T cell leukemia and other tumors, and possibly for inhibiting the uptake and/or replication of HIV in connection with AIDS. In addition, said compounds are of potential value in treating certain diseases of the brain (such as epilepsy) and of the skeletal muscle (such as muscular atrophy). In this connection, the compounds according to the invention are characterized by low toxicity, good enteral absorption (high bioavailability), great therapeutic breadth and the absence of significant side-effects.

The invention furthermore relates to a method for treating mammals, including humans, which/who are suffering from one of the abovementioned diseases. The method is characterized by the fact that a therapeutically effective and pharmacologically tolerated quantity of one or more of the compounds according to the invention is administered to the affected mammal.

The invention furthermore relates to the compounds according to the invention for use in the treatment and/or prophylaxis of diseases, in particular said diseases.

The invention likewise relates to the use of the compounds according to the invention for producing drugs which are employed for the treatment and/or prophylaxis of said diseases.

The invention furthermore relates to drugs for the treatment and/or prophylaxis of the said diseases, which drugs comprise one or more of the compounds according to the invention.

The invention furthermore relates to a commercial product which consists of a customary secondary packaging means, a primary packaging means (for example an ampoule or a blister pack) which contains a drug, and, if desired, a patient information leaflet, with the drug exhibiting an antagonistic effect toward type 7 cyclic nucleotide phosphodiesterases (PDE7) and leading to the attenuation of the symptoms of diseases which are associated with type 7 cyclic nucleotide phosphotodiesterases, and with reference being made, on the secondary packaging means and/or on the patient information leaflet of the commercial product, to the suitability of the drug for use in the prophylaxis or treatment of diseases which are associated with type 7 cyclic nucleotide phosphoesterases, and with the drug comprising one or more compounds of the formula I according to the invention or a pharmacologically tolerated salt thereof. The secondary packaging means, the primary packaging means containing the drug and the patient information leaflet otherwise correspond to what the skilled person would regard as being the standard for drugs of this nature.

The drugs are produced using methods with which the skilled person is familiar. When employed as drugs, the compounds according to the invention (=active compounds) are either used as such or, preferably, in combination with suitable pharmaceutical auxiliary substances, for example in the form of tablets, sugar-coated tablets, capsules, suppositories, plasters, emulsions, suspensions, gels or solutions, with the content of active compound advantageously being between 0.1 and 95%.

On the basis of his specialist knowledge, the skilled person is familiar with the auxiliary substances which are suitable for the desired drug formulations. In addition to solvents, gel formers, ointment bases and other active compound excipients, it is also possible, for example, to use antioxidants, dispersing agents, emulsifiers, preservatives, solubilizers or permeation promoters.

For the treatment of diseases of the respiratory tract, the compounds according to the invention are preferably also administered by inhalation, preferably in the form of an aerosol, with the aerosol particles of solid, liquid or mixed composition having a diameter of from 0.5 to 10 μm, advantageously of from 2 to 6 μm.

The aerosol can be produced, for example, using pressure-driven nozzle nebulizers or ultrasonic nebulizers, advantageously, however, using propellant gas-driven metered aerosols or by means of the propellant gas-free use of micronized active compounds from inhalation capsules.

Depending on the inhalation system employed, the administration forms also contain, in addition to the active compounds, the requisite auxiliary substances, for example propellant gases (e.g. Frigen in the case of metered aerosol), surface-active substances, emulsifiers, stabilizers, preservatives, aromatizing agents, fillers (e.g. lactose in the case of powder inhalers) and, where appropriate, additional active compounds.

For the purposes of inhalation, there are available a larger number of appliances which can be used to generate aerosols of optimal particle size and administer them using an inhalation technique which is as appropriate as possible for the patient. In addition to using attachments (spacers and expanders) and pear-shaped containers (e.g. Nebulator® and Volumatic®), and also automatic spray puff releasers (Autohaler®) for metered aerosols, a number of technical solutions are available, particularly in the case of the powder inhalers (e.g. Diskhaler®, Rotadisk®, Turbohaler® or the inhaler described in European Patent Application 0 505 321), which technical solutions can be used to achieve optimal administration of the active compound.

For the treatment of dermatoses, the compounds according to the invention are used, in particular, in the form of drugs which are suitable for topical administration. For producing the drugs, the compounds according to the invention (=active compounds) are preferably mixed with suitable pharmaceutical auxiliary substances and further processed into suitable medicinal formulations. Suitable medicinal formulations which may be mentioned by way of example are powders, emulsions, suspensions, sprays, oils, ointments, greasy ointments, creams, pastes, gels and solutions.

The drugs according to the invention are produced using methods which are known per se. The active compounds are dosed in customary quantities. Thus, topical application forms (such as ointments) for the treatment of dermatoses comprise the active compounds at a concentration of, for example, 0.1–99%. The dose for administration by inhalation is customarily between 0.1 and 3 mg per day. The customary dose in the case of systemic therapy (oral or i. v.) is between 0.03 and 3 mg per kilogram and day.

Bi Logical Investigations
Inhibiting the Activity of PDE7

Cloning and expression of PDE7: The cDNAs for PDE7A1 and 7A2 (GenBank Acc-: L12052 and u67932, respectively) were isolated, using RT-PCR, from total cellular RNA derived from the T cell line CCRF-CEM and cloned into the cloning vector pCR2.1 (Invitrogen, Groningen, NL) under standard conditions (the manufacturer's instructions). For expression in insect cells, the cDNAs were subcloned into the baculo expression vector pCRBac (Invitrogen, Groningen, NL).

The recombinant baculoviruses were prepared, by means of homologous recombination in SF9 insect cells, by cotransfecting the plasmids containing baculovirus DNA (wild type, wt) Bac-N-Blue (Invitrogen, Groningen, NL) for PDE7A1 and containing Baculo-Gold DNA (Pharmingen, Hamburg) using a standard protocol (Pharmingen, Hamburg). Wt virus-free recombinant virus supernatants were selected using plaque assay methods. After that, high-titre virus supernatants were prepared by amplifying 3 times.

For determining the enzyme activities, the PDEs were expressed in SF21 cells by infecting $2 \times 10^6$ cells/ml with an MOI (multiplicity of infection) ≈5 in serum-free SF900 medium (Life Technologies, Paisley, UK) in spinner flasks. The cells were cultured at 28° C., and at a rotationall speed of 75 rpm, for 48 hours, after which they were pelleted for 5–10 min at 1000 g and 4° C. and then resuspended in 1×PBS at a concentration of $1-3 \times 10^6$ cells/ml. The protein content was determined by the Bradford method (BioRad, Munich) using BSA as the standard.

The SF21 insect cells are resuspended, at a concentration of approx. $10^7$ cells/ml, in ice-cold (4° C.) homogenization buffer (20 mM Tris, pH 8.2, containing the following additions: 140 mM NaCl, 3.8 mM KCl, 1 mM EGTA, 1 mM $MgCl_2$, 1 mM β-mercaptoethanol, 2 mM benzamidine, 0.4 mM Pefablock, 10 $\mu$M leupeptin, 10 $\mu$M pepstatin A, 5 $\mu$M trypsin inhibitor) and disrupted by ultrasonication. The homogenate is then centrifuged for 10 min at 1000×g and the supernatant is stored at −80° C. until subsequent use (see below).

The PDE7 activity was inhibited by said compounds in a modified SPA (scintillation proximity assay) test, supplied by Amersham Pharmacia Biotech (see procedural instructions "Phosphodiesterase [3H]cAMP SPA enzyme assay, code TRKQ 7090"), carried out in 96-well microtitre plates (MTPs). The test volume is 100 $\mu$l and contains 20 mM Tris buffer (pH 7.4), 0.1 mg of BSA (bovine serum albumin)/ml, 5 mM $Mg^{2+}$, 0.5 $\mu$M cAMP (including about 50,000 cpm of [3H]cAMP), 2 $\mu$l of the respective substance dilution in DMSO and sufficient recombinant PDE7A1 (1000×g supernatant, see above) to ensure that 15–20% of cAMP is converted under said experimental conditions. After a pre-incubation of 5 min at 37° C., the reaction is started by adding a substrate (cAMP) and the assays are incubated for a further 15 min; after that, they are stopped by adding SPA beads (50 $\mu$l). In accordance with the manufacturer's instructions, the SPA beads had previously been resuspended in water and diluted 1:3 (v/v) and added to IBMX (3 mM). After the beads have been sedimented (>30 min), the MTPs are analyzed in commercially available measuring appliances and the corresponding $IC_{50}$ values of the compounds for the inhibition of PDE7 activity are determined from concentration-effect curves by means of non-linear regression.

The inhibitory values [inhibitory concentration as $-\log IC_{50}$ (mol/l)] which were determined for the compounds according to the invention are shown in the following table 1, in which the numbers of the compounds correspond to the numbers of the examples.

TABLE 1

| Inhibition of PDE7 activity | |
| --- | --- |
| Compound | $-\log IC_{50}$ |
| 1a | 7.49 |
| 1b | 6.91 |
| 2a | 6.53 |
| 4c | 6.59 |
| 4e | 6.41 |
| 6h | 6.61 |
| 6m | 6.42 |

What is claimed is:

1. A compound of the formula I (I)

[Structure of formula I: isoquinoline core with R1, R2, R', R'', Ar substituents]

in which either
R1 denotes hydrogen, and
R2 denotes fluorine, chlorine, bromine, cyano, trifluoromethyl or phenoxy, or
R1 denotes hydrogen, fluorine, chlorine, bromine, trifluoromethyl or cyano, and
R2 denotes hydrogen,
R' and R'' both denote hydrogen or together represent a bond, and
Ar represents a phenyl radical of the formulae IIa, IIb, or IIc (IIa)

[Structure of formula IIa]

(IIb)

[Structure of formula IIb]

(IIc)

[Structure of formula IIc]

in which
R3 denotes hydrogen, hydroxyl, nitro, amino, carboxyl, aminocarbonyl, 1–4C-alkoxy, trifluoromethoxy, 1–4C-alkoxycarbonyl or mono- or di-1–4C-alkylaminocarbonyl,
R4 represents 1–4C-alkyl, naphthalenyl, 5-dimethylaminonaphthalen-1-yl, phenylethen-2-yl, 3,5-dimethylisoxazol-4-yl, 5-chloro-3-methylbenzo[b]thiophen-2-yl, 6-chloro-imidazo[2,1b]-thiazol-5-yl, or represents a phenyl or thiophene radical which is unsubstituted or is substituted by one or more identical or different radicals selected from the group halogen, cyano, 1–4C-alkyl, trifluoromethyl, 1–4C-alkoxy which is substituted entirely or mainly by fluorine, 1–4C-alkoxy, 1–4C-alkylcarbonylamino, 1–4C-alkoxycarbonyl, phenylsulfonyl or isoxazolyl, or a hydrate, solvate, salt, hydrate of a salt, or solvate of a salt thereof.

2. A compound of the formula I*

(I*)

[Structure of formula I*]

in which either
R1 denotes hydrogen, and
R2 denotes fluorine, chlorine, bromine, cyano, trifluoromethyl or phenoxy, or
R1 denotes hydrogen, fluorine, chlorine, bromine, trifluoromethyl or cyano, and
R2 denotes hydrogen, and
Ar represents a phenyl radical of the formulae IIa or IIb (IIa)

[Structure of formula IIa]

(IIb)

[Structure of formula IIb]

in which
R3 denotes hydrogen, hydroxyl, nitro, amino, carboxyl, aminocarbonyl, 1–4C-alkoxy, trifluoromethoxy, 1–4C-alkoxycarbonyl or mono- or di-1–4C-alkylaminocarbonyl,
R4 represents 1–4C-alkyl, naphthalenyl, 5-dimethylaminonaphthalen-1-yl, phenylethen-2-yl, 3,5-dimethylisoxazol-4-yl, 5-chloro-3-methylbenzo[b]thiophen-2-yl, 6-chloro-imidazo[2,1b]-thiazol-5-yl, or represents a phenyl or thiophene radical which is unsubstituted or is substituted by one or more radicals selected from the group halogen, cyano, 1–4C-alkyl, trifluoromethyl, 1–4C-alkoxy which is substituted entirely or mainly by fluorine, 1–4C-alkoxy, 1–4C-alkylcarbonylamino, 1–4C-alkoxycarbonyl, phenylsulfonyl or isoxazolyl, or a hydrate, solvate, salt, hydrate of a salt, or solvate of a salt thereof.

3. A compound of the formula I as claimed in claim 1, in which
R1 is in the 5-position and denotes fluorine, chlorine, bromine, trifluoromethyl or cyano, and R2 denotes hydrogen, R' and R" both denote hydrogen, and Ar represents a phenyl radical of the formulae IIa or IIb, in which R3 denotes hydrogen, hydroxyl, nitro, amino, carboxyl, aminocarbonyl, 1–4C-alkoxy, trifluoromethoxy, 1–4C-alkoxycarbonyl or mono- or di-1–4C-alkylaminocarbonyl, R4 represents 1–4C-alkyl, naphthalenyl, 5-dimethylaminonaphthalen-1-yl, phenylethen-2-yl, 3,5-dimethylisoxazol-4-yl, 5-chloro-3-methylbenzo[b]thiophen-2-yl, 6-chloro-imidazo[2,1b]-thiazol-5-yl, or represents a phenyl or thiophene radical which is unsubstituted or is substituted by one or more radicals selected from the group halogen, cyano, 1–4C-alkyl, trifluoromethyl, 1–4C-alkoxy which is substituted entirely or mainly by fluorine, 1–4C-alkoxy, 1–4C-alkylcarbonylamino, 1–4C-alkoxycarbonyl, phenylsulfonyl or isoxazolyl, or a hydrate, solvate, salt, hydrate of a salt, or solvate of a salt thereof.

4. A compound of the formula I as claimed in claim 1, in which either

R1 denotes hydrogen, and

R2 denotes fluorine, chlorine, bromine, cyano, trifluoromethyl or phenoxy, or

R1 is in the 6-position and denotes hydrogen, fluorine, chlorine, bromine, trifluoromethyl or cyano, and R2 denotes hydrogen, R' and R" both denote hydrogen, and Ar represents a phenyl radical of the formula IIc, in which R3 denotes hydrogen, hydroxyl, nitro, amino, carboxyl, aminocarbonyl, 1–4C-alkoxy, trifluoromethoxy, 1–4C-alkoxycarbonyl or mono- or di-1–4C-alkylaminocarbonyl, R4 represents 1–4C-alkyl, naphthalenyl, 5-dimethylaminonaphthalen-1-yl, phenylethen-2-yl, 3,5-dimethylisoxazol-4-yl, 5-chloro-3-methylbenzo[b]thiophen-2-yl, 6-chloro-imidazo[2,1b]-thiazol-5-yl, or represents a phenyl or thiophene radical which is unsubstituted or is substituted by one or more radicals selected from the group halogen, cyano, 1–4C-alkyl, trifluoromethyl, 1–4C-alkoxy which is substituted entirely or mainly by fluorine, 1–4C-alkoxy, 1–4C-alkylcarbonylamino, 1–4C-alkoxycarbonyl, phenylsulfonyl or isoxazolyl, or a hydrate, solvate, salt, hydrate of a salt, or solvate of a salt thereof.

5. A compound of the formula I as claimed in claim 1, in which either

R1 denotes hydrogen, and

R2 denotes fluorine, chlorine, bromine, cyano, trifluoromethyl or phenoxy, or

R1 is in the 6-position and denotes hydrogen, fluorine, chlorine, bromine, trifluoromethyl or cyano, and R2 denotes hydrogen, and R' and R" together represent a bond, and Ar represents a phenyl radical of the formulae IIa or IIb, in which R3 denotes hydrogen, hydroxyl, nitro, amino, carboxyl, aminocarbonyl, 1–4C-alkoxy, trifluoromethoxy, 1–4C-alkoxycarbonyl or mono- or di-1–4C-alkylaminocarbonyl, R4 represents 1–4C-alkyl, naphthalenyl, 5-dimethylaminonaphthalen-1-yl, phenylethen-2-yl, 3,5-dimethylisoxazol-4-yl, 5-chloro-3-methylbenzo[b]thiophen-2-yl, 6-chloro-imidazo[2,1b]-thiazol-5-yl, or represents a phenyl or thiophene radical which is unsubstituted or is substituted by one or more radicals selected from the group halogen, cyano, 1–4C-alkyl, trifluoromethyl, 1–4C-alkoxy which is substituted entirely or mainly by fluorine, 1–4C-alkoxy, 1–4C-alkylcarbonylamino, 1–4C-alkoxycarbonyl, phenylsulfonyl or isoxazolyl, or a hydrate, solvate, salt, hydrate of a salt, or solvate of a salt thereof.

6. A compound of the formula I as claimed in claim 1, in which either

R1 denotes hydrogen, and

R2 denotes fluorine, chlorine or phenoxy, or

R1 denotes hydrogen, fluorine, chlorine or trifluoromethyl, and

R2 denotes hydrogen,

R' and R" both denote hydrogen or together represent a bond, and

Ar represents a phenyl radical of the formulae IIa, IIb or IIc, in which

R3 denotes hydrogen, hydroxyl or 1–4C-alkoxy,

R4 denotes 1–4C-alkyl, naphthalenyl, 5-dimethylaminonaphthalen-1-yl, phenylethen-2-yl, 3,5-dimethylisoxazol-4-yl, 5-chloro-3-methylbenzo[b]thiophen-2-yl, 6-chloro-imidazo[2,1b]-thiazol-5-yl, or represents a phenyl or thiophene radical which is unsubstituted or is substituted by one or more identical or different radicals selected from the group halogen, cyano, 1–4C-alkyl, trifluoromethyl, 1–4C-alkoxy which is substituted entirely or mainly by fluorine, 1–4C-alkoxy, 1–4C-alkylcarbonylamino, 1–4C-alkoxycarbonyl, phenylsulfonyl or isoxazolyl, or a hydrate, solvate, salt, hydrate of a salt, or solvate of a salt thereof.

7. A compound of the formula I as claimed in claim 1, in which either

R1 denotes hydrogen, and

R2 denotes fluorine, chlorine or phenoxy, or

R1 denotes hydrogen, fluorine, chlorine or trifluoromethyl, and

R2 denotes hydrogen,

R' and R" both denote hydrogen or together represent a bond, and

Ar represents a phenyl radical of the formulae IIa, IIb or IIc, in which

R3 denotes hydrogen, hydroxy or methoxy,

R4 denotes isopropyl, naphthalen-2-yl, 5-dimethylaminonaphthalen-1-yl, phenylethen-2-yl, 3,5-dimethylisoxazol-4-yl, 5-chloro-3-methylbenzo[b]thiophen-2-yl, 6-chloro-imidazo [2,1b]-thiazol-5-yl, 3,4-difluorophenyl, 2,6-difluorophenyl, 3-trirluoromethylphenyl, 4-bromophenyl, 4-tert-butylphenyl, 4-trifluoromethoxyphenyl, 2,5-dimethoxyphenyl, 3-chloro-2-methylphenyl, 2-trifluoromethoxyphenyl, 2-chloro-4-trifluoromethylphenyl, 2-chloro-4-fluorophenyl, 4-cyanophenyl, 4-methylphenyl, 4-n-butoxyphenyl, 5-isoxazol-3-yl-thiophen-2-yl, 4-phenylsulfonylthiophen-2-yl, 4-bromo-2,5-dichlorothiophen-3-yl, 4-bromo-5- chlorothiophen-2-yl, or 3-methoxy-4-methoxycarbonylthiophen-2-yl, or a hydrate, solvate, salt, hydrate of a salt, or solvate of a salt thereof.

8. A compound of the formula I as claimed in claim 1, in which

R1 denotes hydrogen, and

R2 denotes fluorine or chlorine,

R' and R" both denote hydrogen, and

Ar represents a phenyl radical of the formula IIa, in which

R3 denotes hydroxyl or methoxy,

R4 denotes isopropyl, naphthalen-2-yl, 5-dimethylaminonaphthalen-1-yl, phenylethen-2-yl, 3,5-dimethylisoxazol-4-yl, 5-chloro-3-methylbenzo[b]thiophen-2-yl, 6-chloro-imidazo[2,1b]-thiazol-5-yl, 3,4-difluorophenyl, 2,6-difluorophenyl, 3-trifluoromethylphenyl, 4-bromophenyl, 4-methylcarbonylaminophenyl, 4-tert-butylphenyl, 4-trifluoromethoxyphenyl, 2,5-dimethoxyphenyl, 3-chloro-2-methylphenyl, 2-trifluoromethoxyphenyl, 2-chloro-4-trifluoromethylphenyl, 2-chloro-4-fluorophenyl, 4-cyanophenyl, 4-methylphenyl, 4-n-butoxyphenyl, 5-isoxazol-3-yl-thiophen-2-yl, 4-phenylsulfonylthiophen-2-yl, 4-bromo-2,5-dichlorothiophen-3-yl, 4-bromo-5-chlorothiophen-2-yl, or 3-methoxy-4-methoxycarbonylthiophen-2-yl, or a hydrate, solvate, salt, hydrate of a salt, or solvate of a salt thereof.

9. A compound of the formula I* as claimed in claim 2, in which either

R1 denotes hydrogen, and

R2 denotes fluorine, chlorine or phenoxy, or

R1 denotes hydrogen, fluorine, chlorine or trifluoromethyl, and

R2 denotes hydrogen, and

Ar represents a phenyl radical of the formulae IIa or IIb, in which

R3 denotes hydrogen or 1–4C-alkoxy,

R4 denotes 1–4C-alkyl, naphthalenyl, 5-dimethylaminonaphthalen-1-yl, phenylethen-2-yl, 3,5-dimethylisoxazol-4-yl, 5-chloro-3-methylbenzo[b]thiophen-2yl, 6-chloro-imidazo[2,1b]-thiazol-5-yl, 3,4-difluorophenyl, 2,5-difluorophenyl, 2,6-difluorophenyl, 3-trifluoromethylphenyl, 4-bromophenyl, 4-methylcarbonylaminophenyl, 4-tert-butylphenyl, 4-trifluoromethoxyphenyl, 2,5-dimethoxyphenyl, 3-chloro-2-methylphenyl, 2-trifluoromethoxyphenyl, 2-chloro-4-trifluoromethylphenyl, 2-chloro-4-fluorophenyl, 4-cyanophenyl, 4-methylphenyl, 4-n-butoxyphenyl, 5-isoxazol-3-yl-thiophen-2-yl, 4-phenylsulfonylthiophen-2-yl, 4-bromo-2,5-dichlorothiophen-3-yl, 4-bromo-5-chlorothiophen-2-yl, or 3-methoxy-4-methoxycarbonylthiophen-2-yl, or a hydrate, solvate, salt, hydrate of a salt, or solvate of a salt thereof.

10. A compound of the formula I* as claimed in claim 2, in which either

R1 denotes hydrogen, and

R2 denotes fluorine, chlorine or phenoxy, or

R1 denotes hydrogen, fluorine, chlorine or trifluoromethyl, and

R2 denotes hydrogen, and

Ar represents a phenyl radical of the formulae IIa or IIb, in which

R3 denotes hydrogen or methoxy,

R4 denotes isopropyl, naphthalen-2-yl, 5-dimethylaminonaphthalen-1-yl, phenylethen-2-yl, 3,5-dimethylisoxazol-4-yl, 5-chloro-3-methylbenzo[b]thiophen-2-yl, 6-chloro-imidazo[2,1b]-thiazol-5-yl, 3,4-difluorophenyl, 2,5-difluorophenyl, 2,6-difluorophenyl, 3-trifluoromethylphenyl, 4-bromophenyl, 4-methylcarbonylaminophenyl, 4-tert-butylphenyl, 4-trifluoromethoxyphenyl, 2,5-dimethoxyphenyl, 3-chloro-2-methylphenyl, 2-trifluoromethoxyphenyl, 2-chloro-4-trifluoromethylphenyl, 2-chloro-4-fluorophenyl, 4-cyanophenyl, 4-methylphenyl, 4-n-butoxyphnxyl, 5-isoxazol-3-yl-thiophen-2-yl, 4-phenylsulfonylthiophen-2-yl, 4-bromo-2,5-dichlorothiophen-3-yl, 4-bromo-5-chlorothiophen-2-yl, or 3-methoxy-4-methoxycarbonylthiophen-2-yl, or a hydrate, solvate, salt, hydrate of a salt, or solvate of a salt thereof.

11. A compound of the formula I* as claimed in claim 2, in which

R1 denotes hydrogen, and

R2 denotes fluorine or chlorine,

Ar represents a phenyl radical of the formula IIa, in which

R3 denotes methoxy,

R4 denotes isopropyl, naphthalen-2-yl, 5-dimethylaminonaphthalen-1-yl, phenylethen-2-yl, 3,5-dimethylisoxazol-4-yl, 5-chloro-3-methylbenzo[b]thiophen-2-yl, 6-chloro-imidazo[2,1b]-thiazol-5-yl, 3,4-difluorophenyl, 2,5-difluorophenyl, 2,6-difluorophenyl, 3-trifluoromethylphenyl, 4-bromophenyl, 4-methylcarbonylaminophenyl, 4-tert-butylphenyl, 4-trifluoromethoxyphenyl, 2,5-dimethoxyphenyl, 3-chloro-2-methylphenyl, 2-trifluoromethoxyphenyl, 2-chloro-4-trifluoromethylphenyl, 2-chloro-4-fluorophenyl, 4-cyanophenyl, 4-methylphenyl, 4-n-butoxyphenyl, 5-isoxazol-3-yl-thiophen-2-yl, 4-phenylsulfonyl-thiophen-2-yl, 4-bromo-2,5-dichlorothiophen-3-yl, 4-bromo-5-chlorothiophen-2-yl, or 3-methoxy-4-methoxycarbonylthiophen-2-yl, or a hydrate, solvate, salt, hydrate of a salt, or solvate of a salt thereof.

12. A pharmaceutical composition which comprises at least one compound of the formula I as claimed in claim 1 or a pharmaceutically acceptable hydrate, solvate, hydrate of a salt or solvate of a salt thereof together with customary pharmaceutical auxiliary and/or carrier substances.

13. A method of treating inflammation associated with bronchial asthma, COPD, dermatoses, psoriasis, atopic dermatitis, glomerulonephritis, autoimmune diabetes, multiple sclerosis, Crohn's disease, ulcerative colitis, conjunctivitis and/or rheumatoid arthritis in a patient comprising administering to said patient in need thereof a therapeutically effective amount of a compound of formula I as claimed in claim 1 or a pharmaceutically acceptable hydrate, solvate, salt, hydrate of a salt or solvate of a salt thereof.

14. The method of claim 13, wherein the inflammation is associated with bronchial asthma, COPD, derrnatoses, psoriasis, atopic dermatitis, Crohn's disease, ulcerative colitis and/or rheumatoid arthritis.

15. The method of claim 13, wherein the inflammation is associated with bronchial asthma and/or COPD.

16. A pharmaceutical composition which comprises at least one compound of the formula I* as claimed in claim 2 or a pharmaceutically acceptable hydrate, solvate, hydrate of a salt or solvate of a salt thereof together with customary pharmaceutical auxiliary and/or carrier substances.

17. A method of treating inflammation associated with bronchial asthma, COPD, dermatoses, psoriasis, atopic dermatitis, glomerulonephritis, autoimmune diabetes, multiple sclerosis, Crohn's disease, ulcerative colitis, conjunctivitis and/or rheumatoid arthritis in a patient comprising administering to said patient in need thereof a therapeutically effective amount of a compound of formula I* as claimed in claim 2 or a pharmaceutically acceptable hydrate, solvate, salt, hydrate of a salt or solvate of a salt thereof.

18. The method of claim 17, wherein the inflammation is associated with bronchial asthma, COPD, dermatoses, psoriasis, atopic dermatitis, Crohn's disease, ulcerative colitis and/or rheumatoid arthritis.

19. The method of claim 17, wherein the inflammation is associated with bronchial asthma and/or COPD.

* * * * *

UNITED STATES PATENT AND TRADEMARK OFFICE
CERTIFICATE OF CORRECTION

PATENT NO. : 6,818,651 B2
DATED : November 16, 2004
INVENTOR(S) : Weinbrenner et al.

It is certified that error appears in the above-identified patent and that said Letters Patent is hereby corrected as shown below:

Column 38,
Line 59, please delete "3,4-diftuorophenyl" and replace with -- 3,4-difluorophenyl --
Line 60, please delete "3-trirluoromethylphenyl" and replace with
-- 3-trifluoromethylphenyl --

Column 39,
Line 45, please delete "5-chloro-3-methylbenzo [b] thiophen-2yl" and replace with
-- 5-chloro-3-methylbenzo [b] thiophen-2-yl --

Column 40,
Line 63, please delete "derrnatoses" and replace with -- dermatoses --

Signed and Sealed this

First Day of March, 2005

JON W. DUDAS
*Director of the United States Patent and Trademark Office*